(12) United States Patent
Tsai et al.

(10) Patent No.: US 8,403,984 B2
(45) Date of Patent: Mar. 26, 2013

(54) APPARATUS AND METHODS FOR COMPACTING AN INTRAOCULAR LENS

(75) Inventors: George Tsai, Mission Viejo, CA (US); Phu Nguyen, Lake Forest, CA (US)

(73) Assignee: Visiogen, Inc., Santa Ana, CA (US)

( * ) Notice: Subject to any disclaimer, the term of this patent is extended or adjusted under 35 U.S.C. 154(b) by 1164 days.

(21) Appl. No.: 11/564,482

(22) Filed: Nov. 29, 2006

(65) Prior Publication Data
US 2008/0125790 A1   May 29, 2008

(51) Int. Cl.
*A61F 2/16* (2006.01)

(52) U.S. Cl. ....... 623/6.2; 606/107; 623/6.11; 623/6.12; 623/6.15

(58) Field of Classification Search .................. 606/107; 623/6.11, 6.12, 6.15, 6.2
See application file for complete search history.

(56) References Cited

U.S. PATENT DOCUMENTS

| | | | |
|---|---|---|---|
| 4,240,163 A | 12/1980 | Galin |
| 4,409,691 A | 10/1983 | Levy |
| 4,636,210 A | 1/1987 | Hoffer |
| 4,655,770 A | 4/1987 | Gupta et al. |
| 4,666,445 A | 5/1987 | Tillay |
| 4,681,102 A | 7/1987 | Bartell |
| 4,702,244 A | 10/1987 | Mazzocco |
| 4,731,079 A | 3/1988 | Stoy |
| 4,790,847 A | 12/1988 | Woods |
| 4,834,094 A | 5/1989 | Patton et al. |
| 4,842,601 A | 6/1989 | Smith |
| 4,862,885 A | 9/1989 | Cumming |
| 4,883,485 A | 11/1989 | Patel |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,963,148 A | 10/1990 | Sulc et al. |
| 4,994,082 A | 2/1991 | Richards et al. |
| 5,098,439 A | 3/1992 | Hill et al. |
| 5,123,905 A | 6/1992 | Kelman |
| 5,171,319 A | 12/1992 | Keates et al. |
| 5,190,552 A | 3/1993 | Kelman |

(Continued)

FOREIGN PATENT DOCUMENTS

| | | |
|---|---|---|
| DE | 19501444 | 7/1996 |
| DE | 10015472 | 11/2001 |

(Continued)

OTHER PUBLICATIONS

U.S. Appl. No. 12/258,339, filed Oct. 24, 2008.

(Continued)

*Primary Examiner* — Gary Jackson
*Assistant Examiner* — Kevin Everage
(74) *Attorney, Agent, or Firm* — Visiogen, Inc.

(57) ABSTRACT

Disclosed are apparatus for delivering an accommodating intraocular lens to an eye. One apparatus includes an injector with a longitudinal injection passage that has a longitudinal injection axis. The apparatus also includes an accommodating intraocular lens having two interconnected viewing elements. The injector has a member for moving the lens into the injection passage of the apparatus. The accommodating intraocular lens has a longitudinal bisection axis and is initially disposed within the injector with the longitudinal bisection axis at an angle which is non-parallel and non-perpendicular to the injection axis. Additional apparatus and methods are disclosed as well.

24 Claims, 22 Drawing Sheets

U.S. PATENT DOCUMENTS

| | | |
|---|---|---|
| 5,190,553 A | 3/1993 | Kanert et al. |
| 5,275,604 A | 1/1994 | Rheinish et al. |
| 5,275,623 A | 1/1994 | Sarfarazi |
| 5,281,227 A | 1/1994 | Sussman |
| 5,326,347 A | 7/1994 | Cumming |
| 5,354,335 A | 10/1994 | Lipshitz et al. |
| 5,425,734 A | 6/1995 | Blake |
| 5,443,506 A | 8/1995 | Garabet |
| 5,468,246 A | 11/1995 | Blake |
| 5,474,562 A | 12/1995 | Orchowski |
| 5,476,514 A | 12/1995 | Cumming |
| 5,494,484 A | 2/1996 | Feingold |
| 5,496,328 A | 3/1996 | Nakajima et al. |
| 5,496,366 A | 3/1996 | Cumming |
| 5,499,987 A | 3/1996 | Feingold |
| 5,507,806 A | 4/1996 | Blake |
| 5,562,731 A | 10/1996 | Cumming |
| 5,578,081 A | 11/1996 | McDonald |
| 5,582,614 A | 12/1996 | Feingold |
| 5,607,472 A | 3/1997 | Thompson |
| 5,616,148 A | 4/1997 | Eagles et al. |
| 5,620,450 A | 4/1997 | Eagles et al. |
| 5,643,275 A | 7/1997 | Blake |
| 5,653,754 A | 8/1997 | Nakajima et al. |
| 5,674,282 A | 10/1997 | Cumming |
| 5,728,102 A | 3/1998 | Feingold |
| 5,735,858 A | 4/1998 | Makker et al. |
| 5,772,667 A | 6/1998 | Blake |
| 5,800,442 A | 9/1998 | Wolf et al. |
| 5,807,400 A | 9/1998 | Chambers et al. |
| 5,860,984 A | 1/1999 | Chambers et al. |
| 5,873,879 A | 2/1999 | Figueroa et al. |
| 5,876,440 A | 3/1999 | Feingold |
| 5,902,307 A | 5/1999 | Feingold et al. |
| 5,921,989 A | 7/1999 | Deacon et al. |
| 5,928,245 A | 7/1999 | Wolf et al. |
| 5,941,886 A | 8/1999 | Feingold |
| 5,944,725 A | 8/1999 | Cicenas et al. |
| 5,947,975 A | 9/1999 | Kikuchi et al. |
| 5,968,094 A | 10/1999 | Werblin et al. |
| 5,984,962 A | 11/1999 | Anello et al. |
| 6,010,510 A | 1/2000 | Brown et al. |
| 6,013,101 A | 1/2000 | Israel |
| 6,056,758 A | 5/2000 | Vidal et al. |
| 6,083,230 A | 7/2000 | Makker et al. |
| 6,106,554 A | 8/2000 | Bretton |
| 6,117,171 A | 9/2000 | Skottun |
| 6,129,733 A | 10/2000 | Brady et al. |
| 6,162,229 A | 12/2000 | Feingold et al. |
| 6,176,878 B1 | 1/2001 | Gwon et al. |
| 6,179,843 B1 | 1/2001 | Weiler |
| 6,197,058 B1 | 3/2001 | Portney |
| 6,197,059 B1 | 3/2001 | Cumming |
| 6,203,549 B1 | 3/2001 | Waldock |
| 6,217,612 B1 | 4/2001 | Woods |
| 6,228,094 B1 | 5/2001 | Erdman |
| 6,231,603 B1 | 5/2001 | Lang et al. |
| 6,258,123 B1 | 7/2001 | Young et al. |
| 6,280,449 B1 | 8/2001 | Blake |
| 6,280,471 B1 | 8/2001 | Peyman et al. |
| RE37,387 E | 9/2001 | Brady et al. |
| 6,283,975 B1 | 9/2001 | Glick et al. |
| 6,299,641 B1 | 10/2001 | Woods |
| 6,334,862 B1 | 1/2002 | Vidal et al. |
| 6,406,481 B2 | 6/2002 | Feingold et al. |
| 6,423,094 B1 | 7/2002 | Sarfarazi |
| 6,443,985 B1 | 9/2002 | Woods |
| 6,447,519 B1 | 9/2002 | Brady et al. |
| 6,450,642 B1 | 9/2002 | Jethmalani et al. |
| 6,454,802 B1 | 9/2002 | Bretton et al. |
| 6,464,725 B2 | 10/2002 | Skottun |
| 6,468,282 B2 | 10/2002 | Kikuchi et al. |
| 6,488,708 B2 | 12/2002 | Sarfarazi |
| 6,497,708 B1 | 12/2002 | Cumming |
| 6,500,181 B1 | 12/2002 | Portney |
| 6,503,275 B1 | 1/2003 | Cumming |
| 6,503,276 B2 | 1/2003 | Lang et al. |
| 6,551,354 B1 | 4/2003 | Ghazizadeh et al. |
| 6,558,420 B2 | 5/2003 | Green |
| 6,605,093 B1 | 8/2003 | Blake |
| 6,761,737 B2 | 7/2004 | Zadno-azizi et al. |
| 6,764,511 B2 | 7/2004 | Zadno-azizi et al. |
| 6,786,934 B2 | 9/2004 | Zadno-azizi et al. |
| 6,818,158 B2 | 11/2004 | Pham et al. |
| 6,846,326 B2 | 1/2005 | Zadno-azizi et al. |
| 6,858,040 B2 | 2/2005 | Nguyen et al. |
| 6,884,261 B2 | 4/2005 | Zadno-azizi et al. |
| 6,899,732 B2 | 5/2005 | Zadno-azizi et al. |
| 6,923,815 B2 | 8/2005 | Brady et al. |
| 7,041,134 B2 | 5/2006 | Nguyen et al. |
| 7,087,080 B2 | 8/2006 | Zadno-azizi et al. |
| 7,097,660 B2 | 8/2006 | Portney |
| 7,118,596 B2 | 10/2006 | Zadno-azizi et al. |
| 7,125,422 B2 | 10/2006 | Woods et al. |
| 7,198,640 B2 | 4/2007 | Nguyen |
| 7,226,478 B2 | 6/2007 | Ting et al. |
| 7,452,362 B2 | 11/2008 | Zadno-azizi et al. |
| 7,452,378 B2 | 11/2008 | Zadno-azizi et al. |
| 7,615,056 B2 | 11/2009 | Ayton et al. |
| 7,645,300 B2 | 1/2010 | Tsai |
| 2001/0012964 A1 | 8/2001 | Lang et al. |
| 2001/0020171 A1 | 9/2001 | Heyman et al. |
| 2002/0002404 A1 | 1/2002 | Sarfarazi |
| 2002/0004682 A1 | 1/2002 | Zhou et al. |
| 2002/0077633 A1 | 6/2002 | Kikuchi et al. |
| 2002/0082609 A1 | 6/2002 | Green |
| 2002/0138140 A1 | 9/2002 | Hanna |
| 2002/0188351 A1 | 12/2002 | Laguette |
| 2002/0193876 A1 | 12/2002 | Lang et al. |
| 2003/0018384 A1 | 1/2003 | Valyunin et al. |
| 2003/0078657 A1 | 4/2003 | Zadno-azizi et al. |
| 2003/0078658 A1 | 4/2003 | Zadno-azizi |
| 2003/0109925 A1 | 6/2003 | Ghazizadeh et al. |
| 2003/0114927 A1 | 6/2003 | Nagamoto |
| 2003/0158560 A1 | 8/2003 | Portney |
| 2003/0187504 A1 | 10/2003 | Weinschenk, III et al. |
| 2004/0059343 A1 | 3/2004 | Shearer et al. |
| 2004/0160575 A1* | 8/2004 | Ayton et al. ............... 351/160 R |
| 2005/0182419 A1 | 8/2005 | Tsai |
| 2005/0228401 A1 | 10/2005 | Zadno-Azizi et al. |
| 2005/0234547 A1 | 10/2005 | Nguyen et al. |
| 2005/0251236 A1 | 11/2005 | Jeannin et al. |
| 2006/0100703 A1 | 5/2006 | Evans et al. |
| 2006/0178741 A1 | 8/2006 | Zadno-Azizi et al. |
| 2006/0184244 A1 | 8/2006 | Nguyen et al. |
| 2006/0259139 A1 | 11/2006 | Zadno-Azizi et al. |
| 2006/0271187 A1 | 11/2006 | Zadno-Azizi et al. |
| 2007/0027540 A1 | 2/2007 | Zadno Azizi et al. |
| 2007/0032866 A1 | 2/2007 | Portney |
| 2007/0050023 A1 | 3/2007 | Bessiere et al. |
| 2007/0050025 A1 | 3/2007 | Nguyen et al. |
| 2008/0027461 A1 | 1/2008 | Vaquero et al. |
| 2008/0045971 A1 | 2/2008 | Ayton et al. |
| 2009/0005788 A1 | 1/2009 | Rathert |
| 2009/0030425 A1 | 1/2009 | Smiley et al. |
| 2009/0112313 A1 | 4/2009 | Mentak |
| 2009/0234366 A1 | 9/2009 | Tsai et al. |
| 2010/0076449 A1 | 3/2010 | Tsai |

FOREIGN PATENT DOCUMENTS

| | | |
|---|---|---|
| EP | 0162573 | 11/1985 |
| EP | 0269288 | 6/1988 |
| EP | 0337390 A2 | 10/1989 |
| EP | 0336877 | 10/1993 |
| EP | 1114623 | 11/2001 |
| EP | 1481652 | 12/2004 |
| EP | 1736118 | 12/2006 |
| FR | 2900570 | 11/2007 |
| JP | S61-279241 | 12/1986 |
| JP | 02-126847 | 5/1990 |
| JP | H03-137325 | 6/1991 |
| JP | H09-508810 | 9/1997 |
| WO | WO 95/13022 | 5/1995 |
| WO | WO 96/29956 | 10/1996 |
| WO | WO 98/12969 | 4/1998 |
| WO | WO 99/20206 | 4/1999 |
| WO | WO 99/21513 | 6/1999 |

| | | |
|---|---|---|
| WO | WO 00/21467 | 4/2000 |
| WO | WO 00/27315 | 5/2000 |
| WO | WO 00/61036 | 10/2000 |
| WO | WO 00/66037 | 11/2000 |
| WO | WO 01/19289 | 3/2001 |
| WO | WO 01/34067 | 5/2001 |
| WO | WO 01/64136 | 9/2001 |
| WO | WO 01/66042 | 9/2001 |
| WO | WO 01/87186 | 11/2001 |
| WO | WO 02/071983 | 9/2002 |
| WO | WO 03/015657 | 2/2003 |
| WO | WO 04/000171 | 12/2003 |
| WO | WO 2004/073560 | 9/2004 |
| WO | WO 2005/074838 | 8/2005 |
| WO | WO 2007/080868 | 7/2007 |

OTHER PUBLICATIONS

Tsutomu Hara et al., "Accommodative Intraocular Lens with Spring Action Part 1. Design and Placement in an Excised Animal Eye," Opthalmic Surgery, Feb. 1990, vol. 21, No. 2, pp. 128-133.

International Search Report and Written Opinion of the International Searching Authority, mailed May 6, 2008, in related International application No. PCT/US2007/085813, 16 pp.

International Preliminary Report on Patentability, mailed Jun. 11, 2009, in related International application No. PCT/US2007/085813, 12 pp.

International Search Report and Written Opinion of the International Searching Authority, mailed May 18, 2005, in related international application No. PCT/US2004/004033.

International Search Report and Written Opinion of the International Searching Authority, mailed Jan. 18, 2006, in related international application No. PCT/US2005/002871.

English Translation of Office Action dated Apr. 24, 2009 and issued in related Japanese Patent Application No. 2006-503503.

* cited by examiner

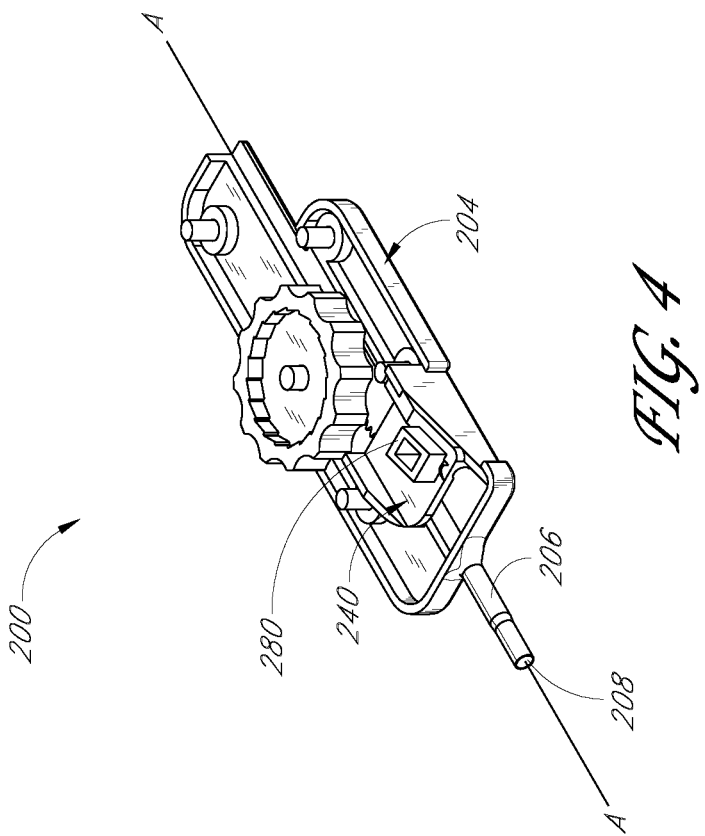
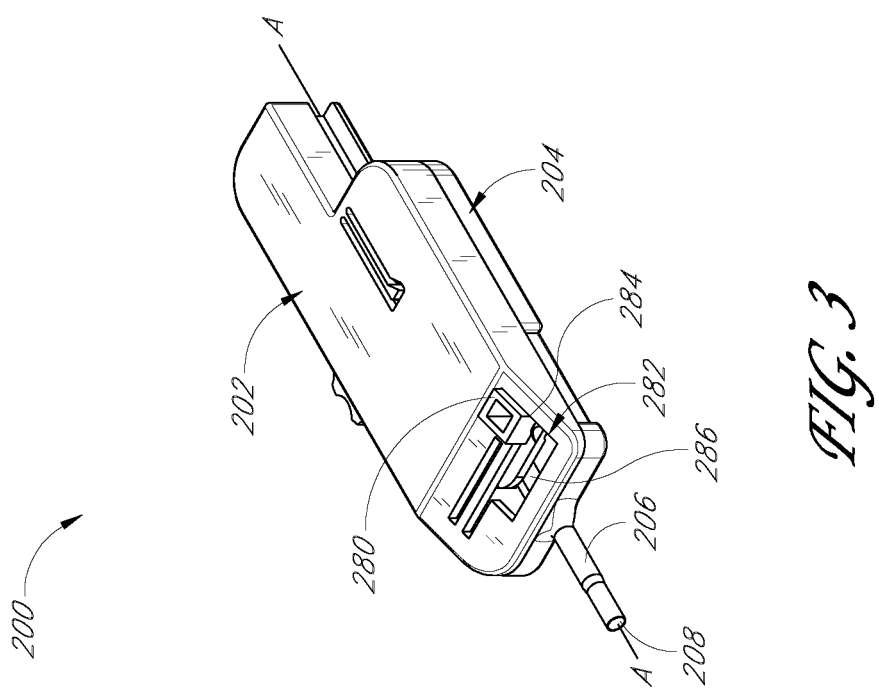

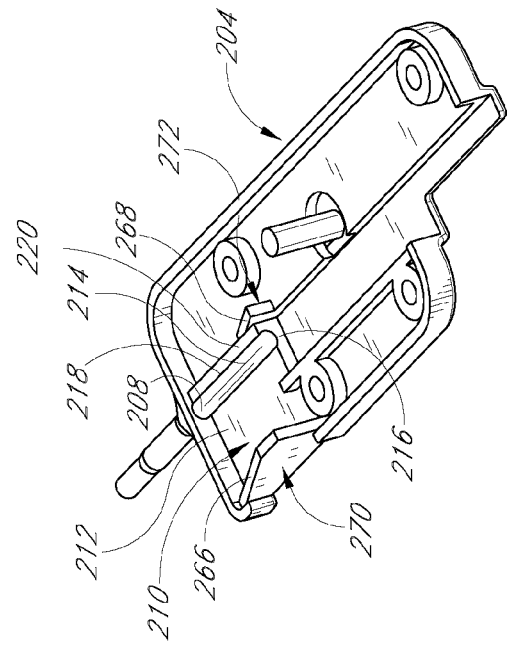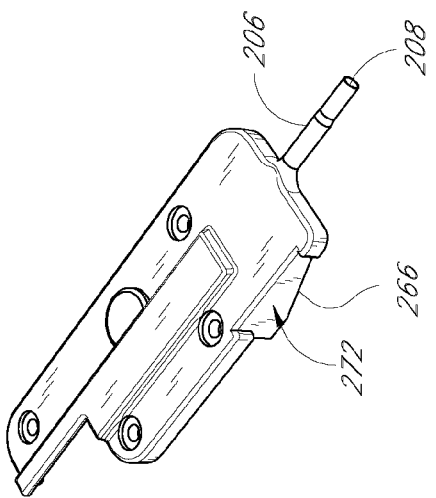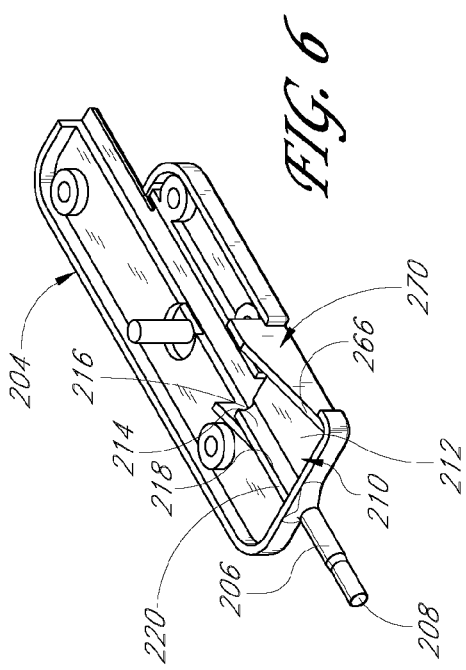

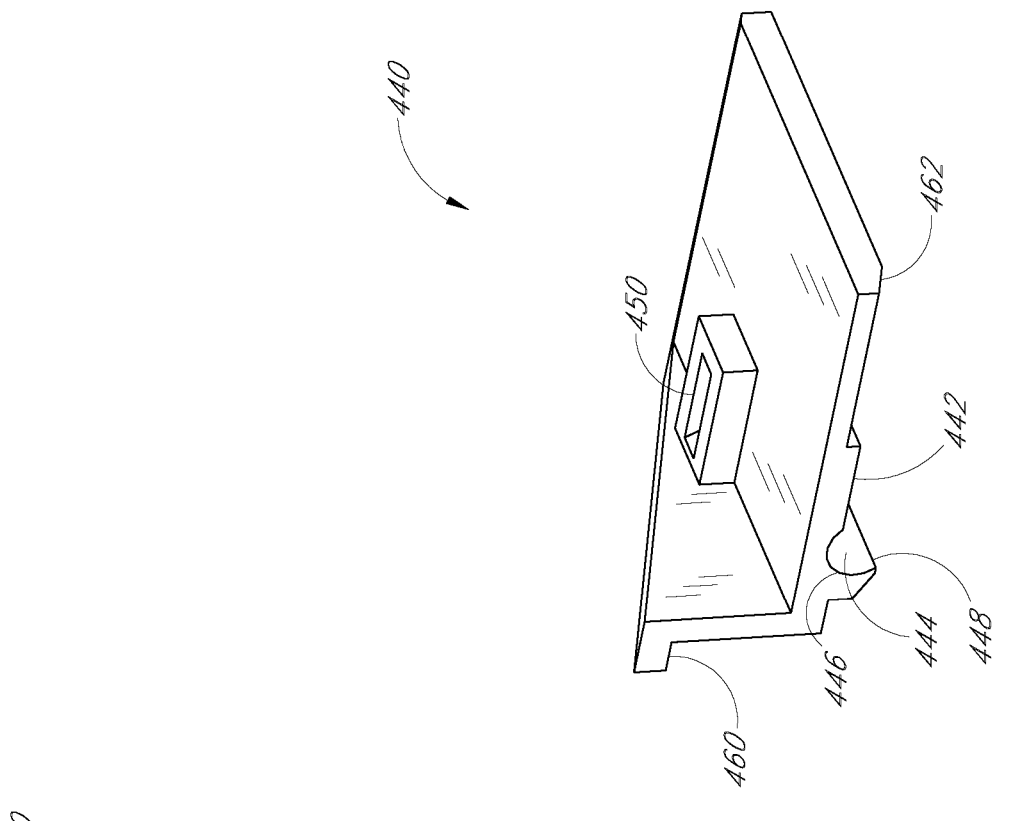
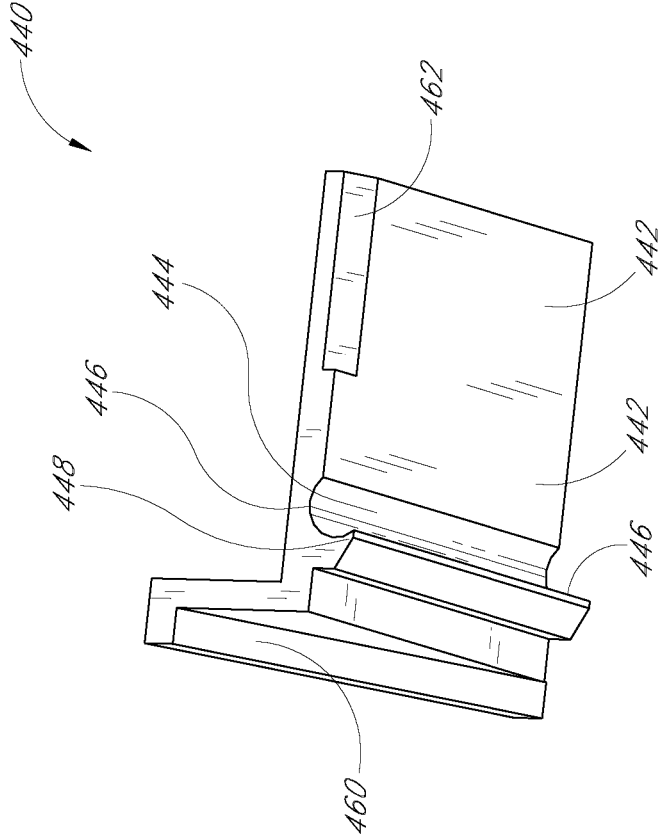

APPARATUS AND METHODS FOR COMPACTING AN INTRAOCULAR LENS

BACKGROUND

1. Field of the Disclosure

Various embodiments disclosed herein pertain to insertion of intraocular lenses into the eye of a patient, as well as methods and devices for preparing an intraocular lens for insertion, and for achieving the insertion itself.

2. Description of the Related Art

Artificial intraocular lenses are often implanted to replace or supplement the natural crystalline lens. Such a lens may be implanted where the natural lens has developed cataracts or has lost elasticity to create a condition of presbyopia. Implantation devices have been developed to roll or fold an intraocular lens, and/or assist in implanting a rolled or folded lens through a small incision in the patient's eye. However, these known implantation devices suffer from various drawbacks, many of which are addressed by certain embodiments disclosed herein.

SUMMARY

One aspect of the disclosure is an apparatus for delivering an accommodating intraocular lens to an eye. In one embodiment, the apparatus comprises an injector with a longitudinal injection passage having a longitudinal injection axis. The apparatus also comprises an accommodating intraocular lens having two interconnected viewing elements. The injector has a member for moving the lens into the injection passage. The lens has a longitudinal bisection axis and is disposed within the injector with the longitudinal bisection axis of the lens at an angle which is non-parallel and non-perpendicular to the injection axis.

Another aspect of the disclosure is a method for preparing an accommodating intraocular lens for delivery to an eye. In one embodiment, the method comprises providing an injector with a longitudinal injection passage having a longitudinal injection axis. The method further comprises providing an accommodating intraocular lens having two interconnected viewing elements and a longitudinal bisection axis. The intraocular lens is disposed within the injector. The method also comprises initiating movement of one viewing element of the intraocular lens relative to the other viewing element thereof in a direction within the injector that is at an angle that is non-parallel and non-perpendicular to the longitudinal bisection axis prior to the movement or non-parallel and non-perpendicular to the longitudinal injection axis prior to the movement. The method also comprises further moving the intraocular lens into the injection passage.

Another aspect of the disclosure is a method for preparing an accommodating intraocular lens for delivery to an eye. In one embodiment, the method comprises providing an injector with a longitudinal injection passage having a longitudinal injection axis and providing an accommodating intraocular lens having first and second interconnected viewing elements and a longitudinal bisection axis. The intraocular lens is disposed within the injector so that the longitudinal bisection axis defines an initial longitudinal axis direction prior to movement of the lens within the injector. The method further comprises applying an initial force to at least one of the viewing elements. The initial force is applied in an initial direction that is at an angle that is non-parallel and non-perpendicular to the initial longitudinal axis direction or non-parallel and non-perpendicular to the longitudinal injection axis. The method also comprises moving the intraocular lens into the injection passage of the injector.

Another aspect of the disclosure is an apparatus for manipulating an accommodating intraocular lens. The accommodating intraocular lens has first and second viewing elements with respective optical axes that are substantially coaxial. The lens also has a longitudinal axis that is substantially perpendicular to the substantially coaxial optical axes. In one embodiment, the apparatus comprises an injector having a first configuration and a second configuration and a lens displacement member that is movable by a user to change the injector from the first configuration to the second configuration. In the first configuration, the intraocular lens is disposed in the injector, and the longitudinal axis of the lens defines an initial direction. In the second configuration, the first and second viewing elements are relatively displaced such that a displacement direction is defined therebetween and such that the optical axes are not substantially coaxial. The initial direction and the displacement direction define between them a non-zero and non-perpendicular angle.

All of these aspects and embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which:

FIG. 3 is a perspective view of one embodiment of an apparatus for compacting and/or inserting an intraocular lens.

FIG. 4 is a perspective view of the apparatus of FIG. 3, with the upper housing portion removed for clarity.

FIG. 6 is a perspective view of the lower housing of the apparatus of FIG. 3.

FIG. 7 is a second perspective view of the lower housing of the apparatus of FIG. 3.

FIG. 8 is a third perspective view of the lower housing of the apparatus of FIG. 3.

FIG. 25 is a perspective view of the upper lens compactor of the apparatus of FIG. 21.

FIG. 26 is a second perspective view of the upper lens compactor of the apparatus of FIG. 21.

DETAILED DESCRIPTION OF CERTAIN PREFERRED EMBODIMENTS

Figure 1:
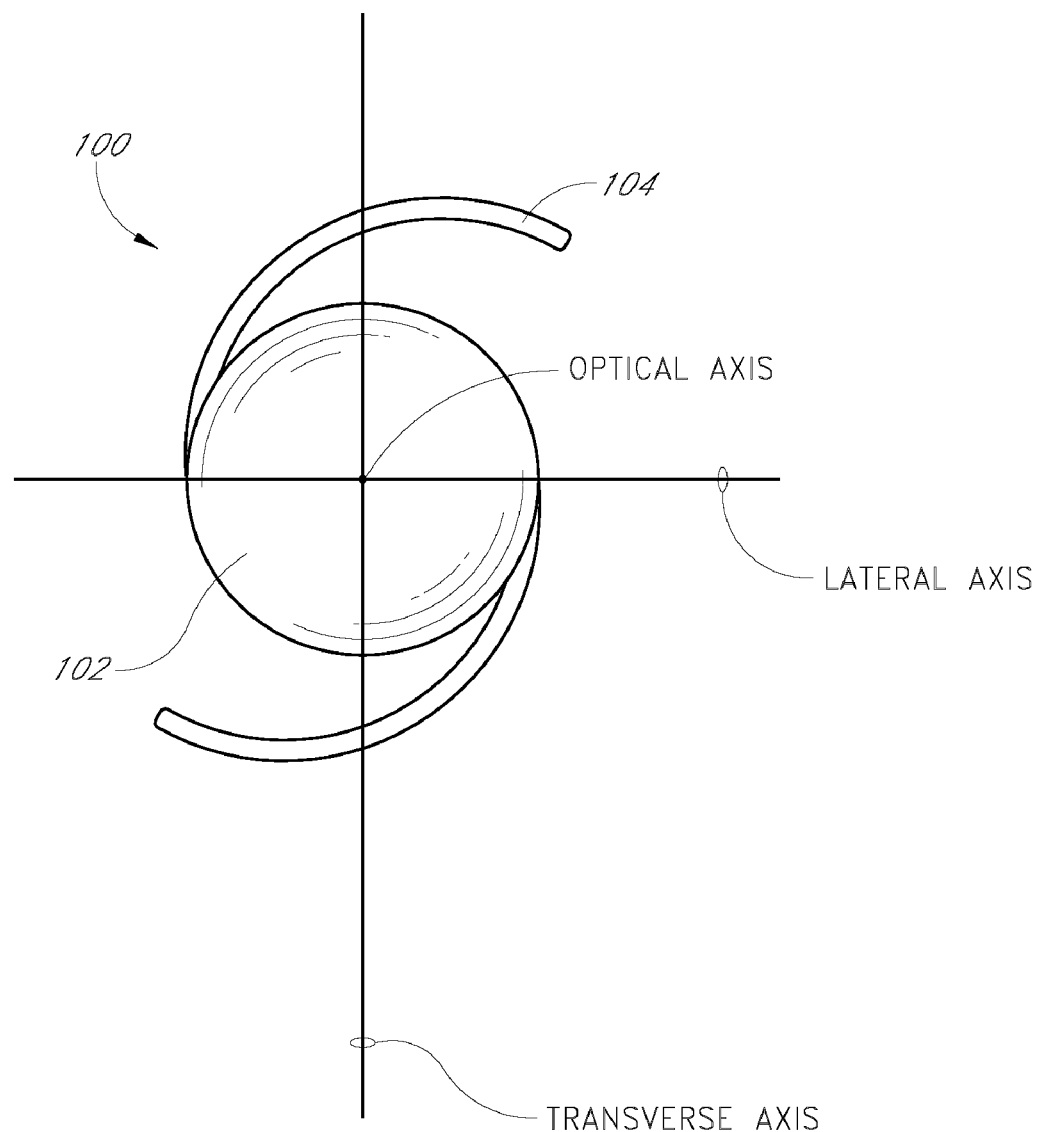
FIG. 1 is a front view of one type of single-lens IOL.
Figure 2:
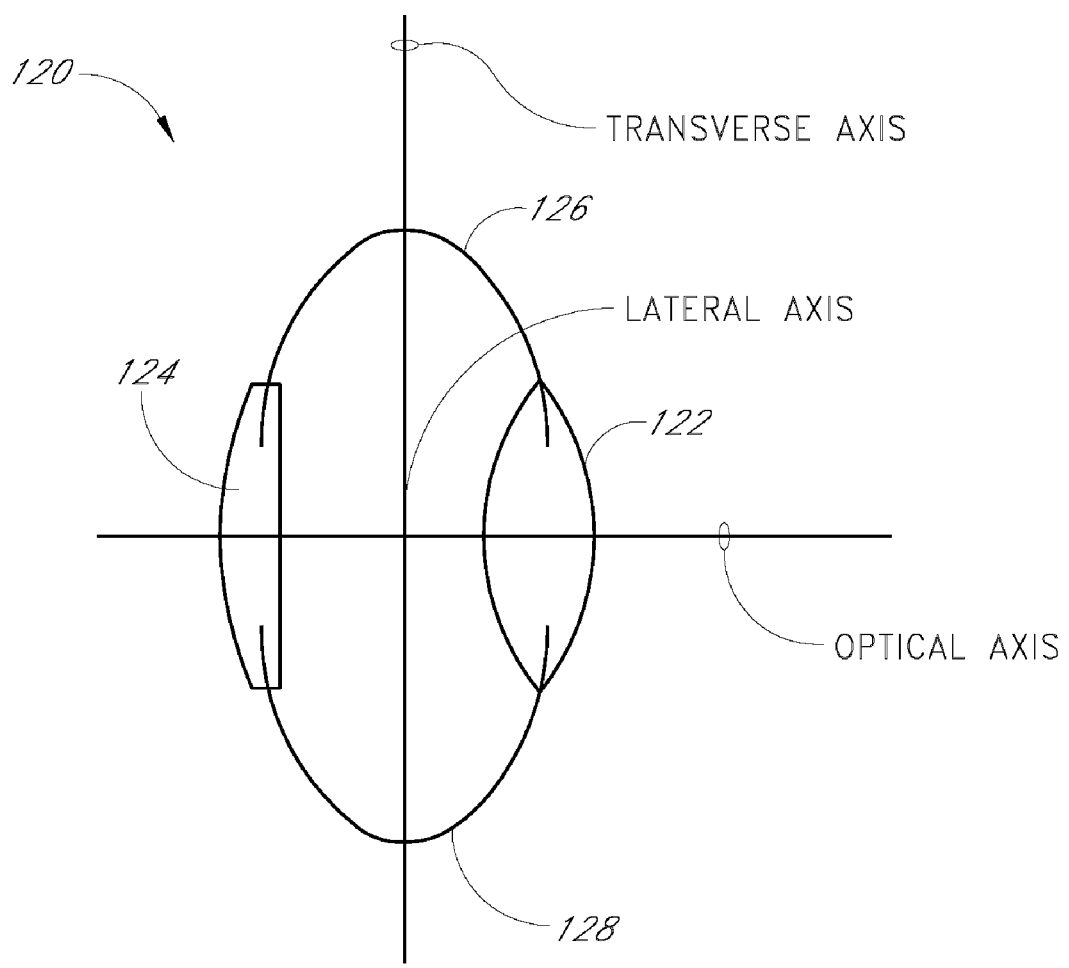
FIG. 2 is a side view of one type of multiple-lens IOL.

FIGS. 1 and 2 depict two known types of intraocular lenses ("IOLs") which are suitable for implantation in a human or animal eye to replace or supplement the natural crystalline lens. An IOL may be implanted, for example, when the natural lens has developed cataracts or has lost elasticity to create a condition of presbyopia.

FIG. 1 is front view of a conventional single-lens IOL 100 comprising an optic 102 to which are connected two or more haptics 104, 106. The optic 102 typically has a refractive power which is selected to replace or adjust the optical performance of the natural lens. The haptics 104, 106 comprise spring-like members which fix the optic in an appropriate location (e.g., inside the ciliary capsule or between the cornea and iris). The IOL 100 has an optical axis generally orthogonal to and centered on the optic; accordingly, in FIG. 1 the optical axis is depicted as a point. In addition, the IOL 100 has a transverse axis orthogonal to the optical axis and passing through arbitrarily chosen top and bottom points of the IOL 100, and a lateral axis orthogonal to the optical and transverse axes, and passing through arbitrarily chosen left and right points of the IOL 100. (The top, bottom, left and right positions are said to be "arbitrarily chosen" because the IOL 100 can be employed in a variety of orientations within the eye, so long as the optical axis is substantially coincident with the optical axis of the eye itself).

FIG. 2 is a side view of a dual- or multiple-lens IOL 120 comprising first and second viewing elements 122, 124 which are interconnected by two or more biasing members 126, 128. One or both of the viewing elements 122, 124 may comprise an optic having refractive power. An IOL of this type is typically implanted in the ciliary capsule such that the biasing members maintain one of the viewing elements 122, 124 against the anterior region of the ciliary capsule, and the other of the viewing elements 122, 124 against the posterior region of the ciliary capsule. The biasing members 126, 128 may be constructed to have spring-like properties to permit the separation between the viewing elements 122, 124 to change in response to changes in the shape of the ciliary capsule that occur during accommodation.

Like the single-lens IOL 100, the multiple-lens IOL 120 has an optical axis, transverse axis and lateral axis, arranged depicted in FIG. 2. In the unstressed configuration shown in FIG. 2, the optical axes of the individual viewing elements 122, 124 are substantially coincident with the optical axis of the IOL 120 itself. However, as discussed below the optical axes of the individual viewing elements 122, 124 may be made non-coincident or non-coaxial during compaction of the IOL 120.

Various types of multiple-lens IOLs are disclosed in U.S. Patent Application Publication No. US 2002/0107568 A1, published on Aug. 8, 2002, titled ACCOMMODATING INTRAOCULAR LENS SYSTEM, and U.S. Patent Application Publication No. US 2003/0074060 A1, published on Apr. 17, 2003, titled METHOD OF PREPARING AN INTRAOCULAR LENS FOR IMPLANTATION. The entire contents of the above-mentioned publications are hereby incorporated by reference herein and made a part of this specification.

Intraocular lenses are typically implanted (after any removal of the natural lens) by first folding or rolling the IOL. The folded/rolled IOL is then inserted into the desired location in the eye by passing the IOL through one or more incisions made in the cornea, sclera and/or ciliary capsule. Once in place, the natural resilience of the IOL causes it to return, either partially or completely, to its original unrolled/unfolded state, whereupon the IOL can function as desired to improve the patient's vision.

FIGS. 3-20 depict one embodiment of an apparatus 200 for compacting and/or inserting an intraocular lens. The depicted apparatus 200 (as well as the other embodiments depicted and/or described herein) may, but need not, be employed to compact and/or insert an intraocular lens, including without limitation IOLs of the types depicted in FIG. 1 or FIG. 2, those described in the publications mentioned above, or any suitable single- or multiple-lens IOL.

Figure 5:
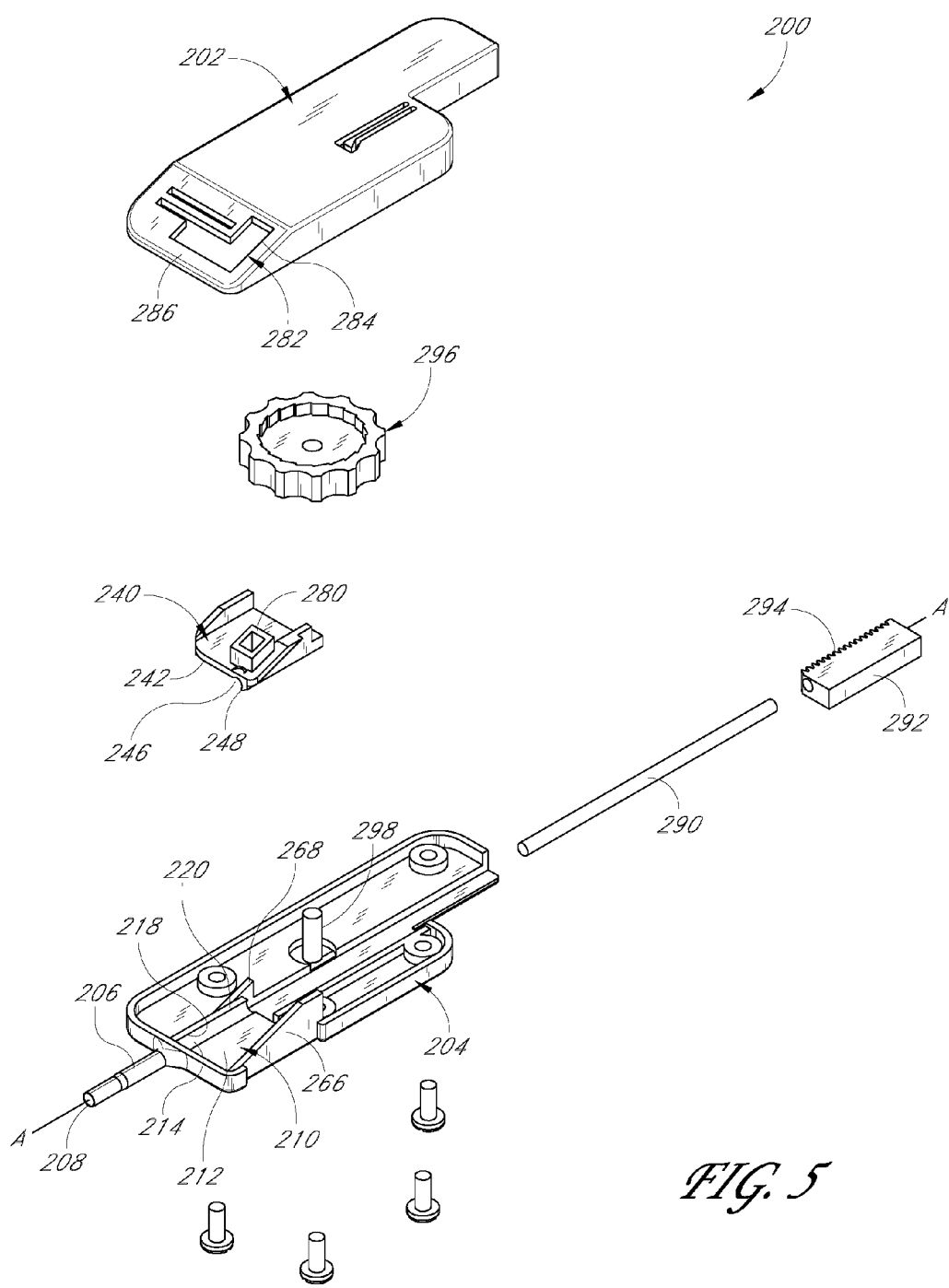
FIG. 5 is an exploded view of the apparatus of FIG. 3.

With reference now to FIGS. 3-5, the apparatus 200 preferably comprises an upper housing 202 and a lower housing 204 which cooperate to enclose and support the components of the apparatus 200. The lower housing 204 preferably forms a delivery probe 206 which in turn defines a delivery lumen 208; both the delivery probe 206 and lumen 208 extend along a longitudinally-oriented delivery or injection axis A-A of the apparatus 200. The lower housing 204 also preferably forms a lower lens compactor or lower compacting element 210 comprising a lower engagement face or wall 212 and a lower insertion channel 214 which extends along the delivery axis A-A.

As best seen in FIG. 8, the lower engagement face 212 preferably comprises a generally flat surface which defines a plane extending generally parallel to (or intercepting) the delivery axis A-A. The lower insertion channel 214 is preferably a partial cylinder in shape, with an inner surface 216 which extends from the lower engagement face 212 to a lower channel edge 218 which preferably extends generally parallel to the delivery axis A-A. The lower insertion channel 214 preferably comprises a partial rearward extension, along the delivery axis A-A, of the inner surface of the delivery lumen 208. From the lower channel edge 218 a lower support surface 220 extends in a direction opposite the lower engagement face 212, while forming a generally flat surface which defines a plane extending preferably generally parallel to the face 212.

Figure 10:
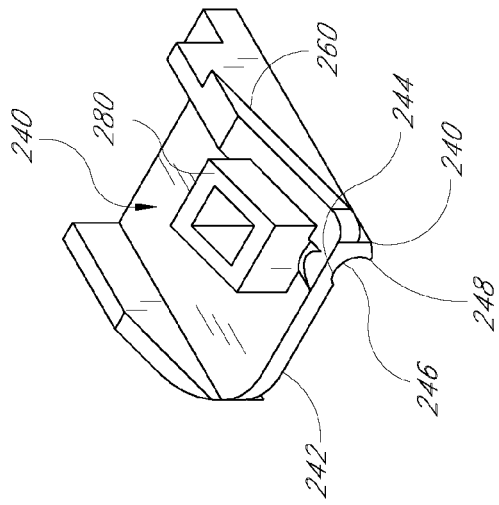
FIG. 10 is a second perspective view of the upper lens compactor of the apparatus of FIG. 3.
Figure 9:
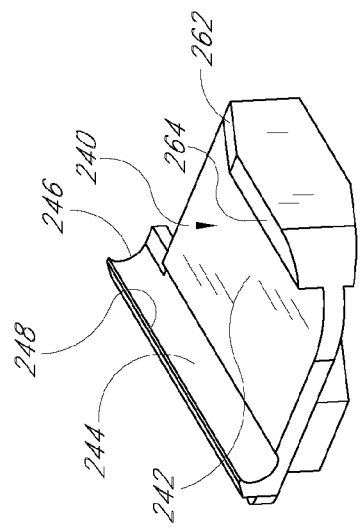
FIG. 9 is a perspective view of the upper lens compactor of the apparatus of FIG. 3.
Figure 20:
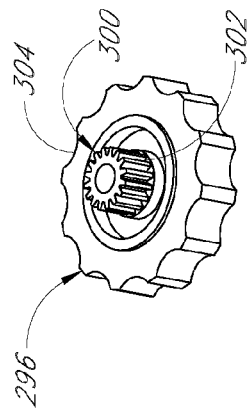
FIG. 20 is a lower perspective view of the pinion wheel of the apparatus of FIG. 3.
Figure 19:
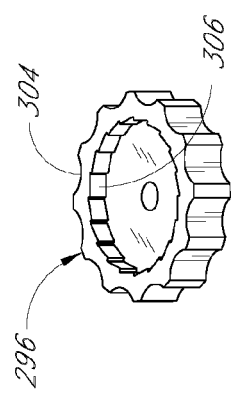
FIG. 19 is an upper perspective view of the pinion wheel of the apparatus of FIG. 3.
Figure 11:
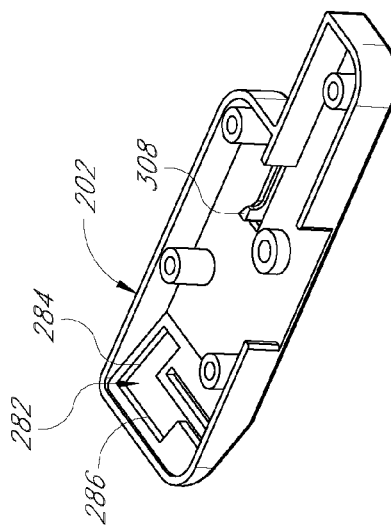
FIG. 11 is a perspective view of the upper housing of the apparatus of FIG. 3.
Figure 13:
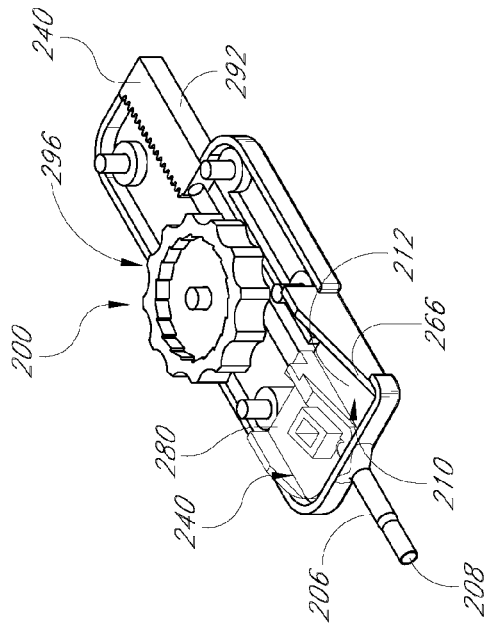
FIG. 13 is a perspective view of the apparatus of FIG. 3, with the upper housing portion removed for clarity, and the upper lens compactor moved to the first compacted position.
Figure 12:
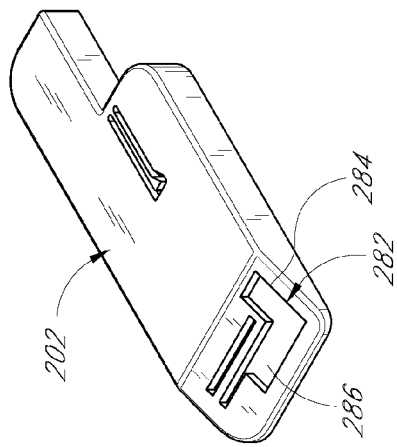
FIG. 12 is a second perspective view of the upper housing of the apparatus of FIG. 3.

Referring again to FIGS. 3-5, and also to FIGS. 9-10, an upper lens compactor 240 is slidably disposed generally above the lower lens compactor 210. The lower and upper lens compactors 210, 240 together form a lens compactor of the apparatus 200. The depicted embodiment of the upper lens compactor 240 forms an upper engagement face 242 which preferably comprises a generally flat surface which, when the upper lens compactor is in position on the lower housing 204, defines a plane extending generally parallel to the delivery axis A-A. The upper lens compactor 240 preferably further comprises an upper insertion channel 244, which is preferably a partial cylinder in shape, with an inner surface 246 which extends from the upper engagement face 242 to an upper channel edge 248 which preferably extends generally parallel to the delivery axis A-A. (Alternatively, the insertion channels 214, 244 may taper inward as they extend forward, thereby forming a truncated cone or another inward-tapering surface upon their convergence when the upper lens compactor 240 is in the second compacted position (see below). Instead of or in addition to such a configuration of the insertion channels 214, 244, the inner surface of the delivery lumen 208 may also taper inward as it extends forward).

In yet another embodiment, the delivery lumen 208 can have a generally oval cross-section (taken orthogonal to the delivery axis), with the channels 214, 244 shaped to have a similarly oval cross-section upon their convergence when the upper lens compactor 240 is in the second compacted position (see below).

The upper lens compactor 240 preferably further comprises first and second upper bearing surfaces 260, 262 disposed on respective opposite sides of the upper engagement face 242 and upper insertion channel 244, as well as a third upper bearing surface 264, which extends forward from the second upper bearing surface 262. The first, second and third upper bearing surfaces 260, 262, 264 preferably comprise generally flat surfaces which extend longitudinally, the first and second upper bearing surfaces 260, 262 being sloped with respect to the upper engagement face 242 and/or delivery axis A-A. The first and second upper bearing surfaces 260, 262 are (at least initially) slidably disposed against similarly-sloped first and second lower bearing surfaces 266, 268 formed on support ribs 270, 272 of the lower housing 204.

With reference now to FIGS. 3-5 and 9-12, the upper lens compactor 240 preferably also forms a compactor actuator 280 which, in the depicted embodiment, comprises a generally vertically-extending member suitable for manipulation by the thumb of a user. The compactor actuator 280 is received in a compactor guide 282 formed in the upper housing 202. In the depicted embodiment, the compactor guide 282 comprises a longitudinal slot 284 and a lateral slot 286 which are joined in an "L" configuration.

The upper and lower bearing surfaces 262, 264, 266, 268, and the compactor actuator 280 and compactor guide 282, coact to permit the upper lens compactor 240 to advance forward and downward from a home position (see FIGS. 3, 4, 15) in which the compactor actuator 280 is rearwardly disposed in the longitudinal slot 284, to a first compacted position (see FIGS. 13, 16) in which the compactor actuator 280 is forwardly disposed in the longitudinal slot 284, but has not yet been advanced laterally. This advancement of the upper lens compactor 240 moves the upper engagement face 242 forward and downward with respect to the lower engagement face 212, thereby reducing the vertical separation between the engagement faces 212, 242. The compactor actuator 280 and compactor guide 282 likewise coact to permit the upper lens compactor 240 to advance laterally from the first compacted position to a second compacted position (see FIGS. 14, 18) in which the compactor actuator 280 is laterally disposed in the lateral slot 286, remote from the longitudinal slot 284.

Figure 15:
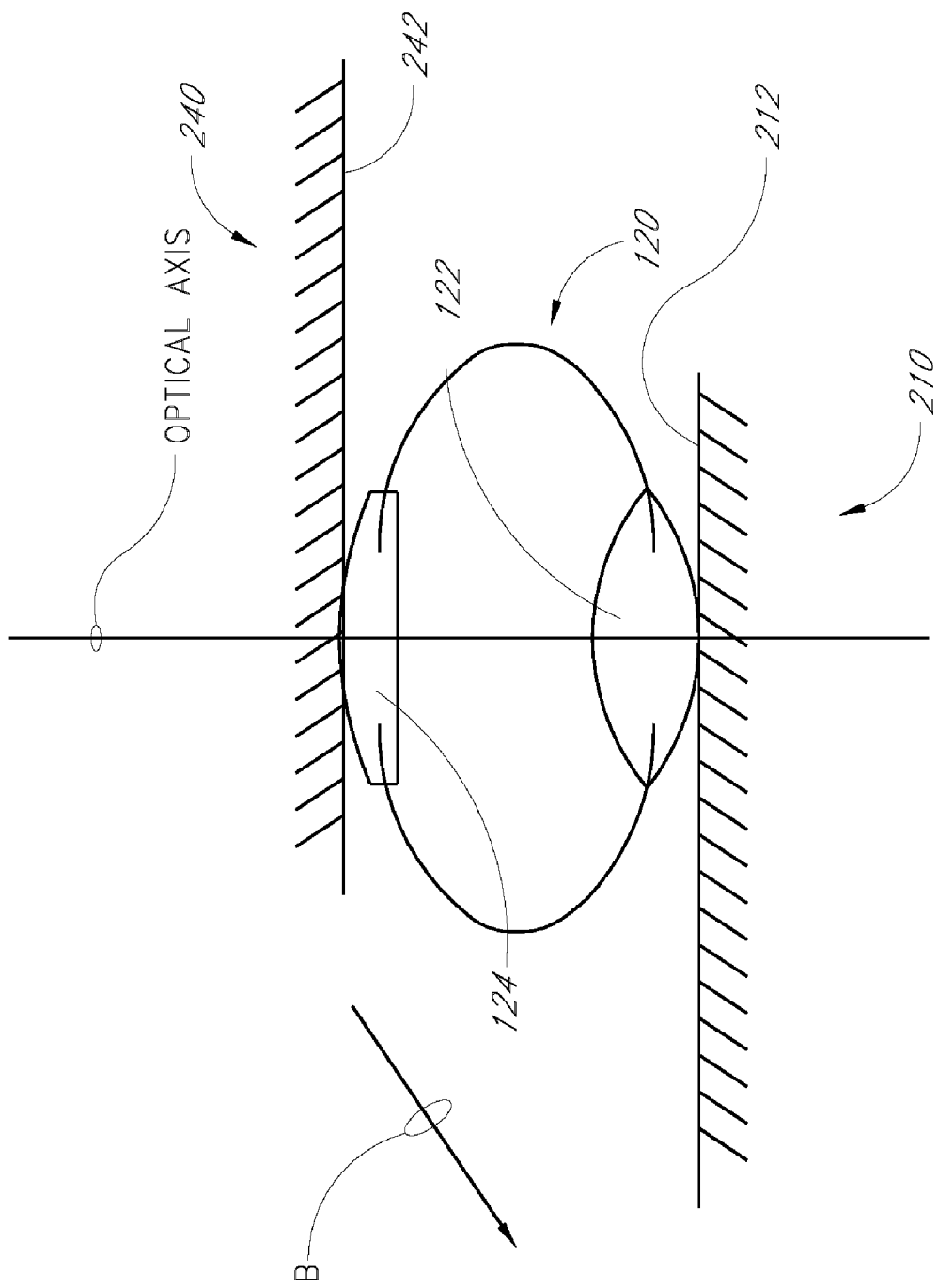
FIG. 15 is a schematic, side cross-sectional view of the apparatus of FIG. 3, with the upper lens compactor in the home position.

FIGS. 15-18 illustrate schematically the operation of the compactors 210, 240 in a circumstance in which a multiple-lens IOL, such as the IOL 120 described above, is stored or placed in the apparatus 200 for subsequent compaction and/or insertion. In FIG. 15, the upper lens compactor 240 is in the home position wherein the upper engagement face 242 is preferably generally parallel to the lower engagement face 212, and the multiple-lens IOL 120 is disposed between the faces 212, 242, preferably in a substantially unstressed condition in which the optical axes of the viewing elements are substantially coincident with each other, and/or with the optical axis of the IOL 120 itself.

Note that the IOL 120 is considered to be substantially unstressed even when the faces 212, 242 compress the viewing elements 122, 124 together somewhat, thereby slightly stressing the biasing members 126, 128. Accordingly, the separation between the faces 212, 242 may be chosen to slightly compress the viewing elements 122, 124 together when the upper lens compactor 240 is in the home position. The IOL 120 is also considered to be substantially unstressed when the faces 212, 242 draw the viewing elements 122, 124 apart somewhat, thereby slightly stressing the biasing members 126, 128. The separation between the faces 212, 242 may therefore be chosen to draw the viewing elements 122, 124 slightly apart when the upper lens compactor 240 is in the home position. The IOL 120 is also considered to be substantially unstressed when the outer faces or other portions of one or both of the viewing elements 122, 124 are deformed or stressed due to adhesion stresses between the faces 212, 242 and the viewing elements (which stresses can arise where the viewing elements 122, 124 comprise optics), as such stresses are relatively minor when viewed in the context of the entire IOL 120.

In the depicted embodiment, the engagement faces 212, 242 comprise generally flat surfaces constructed from a material to which the outer faces of the viewing elements 122, 124 will tend to self-adhere. For example, acetal (sold as DELRIN™) may be employed to construct one or both of the faces 212, 242; this material displays good adhesion properties with many of the materials (e.g., silicone, polyurethanes, hydrogels, acrylics, PVA, styrene-based copolymers) typically employed to construct IOLs. Of course, any other material having good adhesion properties with the contacted portions of the IOL may be employed to form the engagement faces 212, 242.

Figure 16:
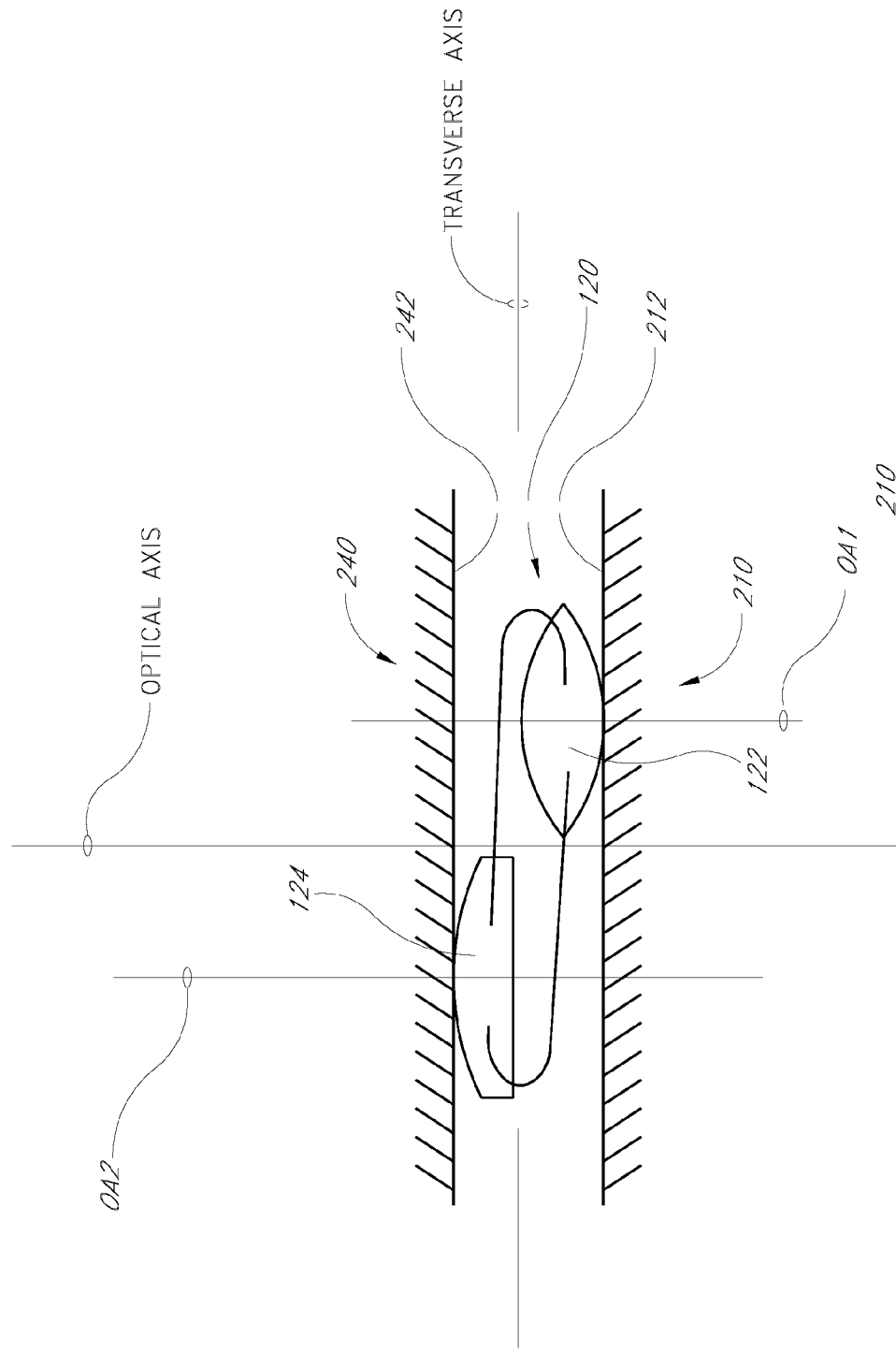
FIG. 16 is a schematic, side cross-sectional view of the apparatus of FIG. 3, with the upper lens compactor in the first compacted position.
Figure 17:
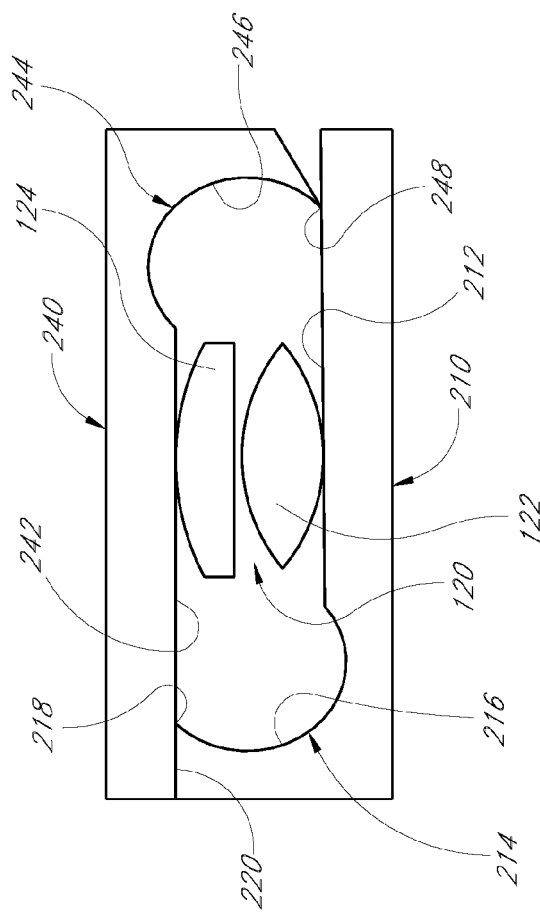
FIG. 17 is a schematic, front cross-sectional view of the apparatus of FIG. 3, with the upper lens compactor in the first compacted position.

From the home position depicted in FIG. 15, the upper engagement face 242 advances forward and downward, as indicated by the arrow B, to the first compacted position shown in FIGS. 16-17. With the upper engagement face in the first compacted position, the IOL 120 assumes a first compacted condition (also shown in FIGS. 16-17) in which the viewing elements 122, 124 are relatively displaced so that they are non-coaxial. (In other words, the optical axes OA1, OA2 of the individual viewing elements are non-coincident with each other, and/or with the optical axis of the IOL 120 itself). In the depicted embodiment, the viewing elements 122, 124 are sufficiently relatively displaced when in the first compacted condition that no portion of the first viewing element 122 overlaps any portion of the second viewing element 124. However, in other embodiments the viewing elements 122, 124 may overlap somewhat (while being nonetheless non-coaxial), as the IOL 120 is viewed along the optical axis, while the IOL 120 is in the first compacted condition. Likewise, in the depicted embodiment no portion of the first viewing element 122 overlaps any portion of the second viewing element 124, as the IOL 120 is viewed along the transverse axis, when the IOL 120 is in the first compacted condition. However, in other embodiments the viewing elements 122, 124 may be sufficiently relatively displaced that they overlap somewhat, as the IOL 120 is viewed along the transverse axis, while the IOL 120 is in the first compacted condition. In still another embodiment, the IOL 120 may have an overall height, as measured along the optical axis, no greater than that of the higher of the first and second viewing elements 122, 124, when the IOL is in the first compacted condition. In the embodiment depicted in FIGS. 16-17, the height of the IOL 120, as measured along the optical axis, is substantially equal to the sum of the heights of the first and second viewing elements 122, 124.

As best seen in FIG. 17, when the upper lens compactor 240 is in the first compacted position, the upper channel edge 248 preferably contacts the lower engagement face 212 and the lower channel edge 218 preferably contacts the upper engagement face 242. In certain embodiments, the lower support surface 220 may also contact the upper engagement face 242. If desired, the IOL 120 may be lubricated when in the first compacted condition, using any suitable lubricant. The lubricant may assist in further compaction of the IOL 120.

Figure 14:
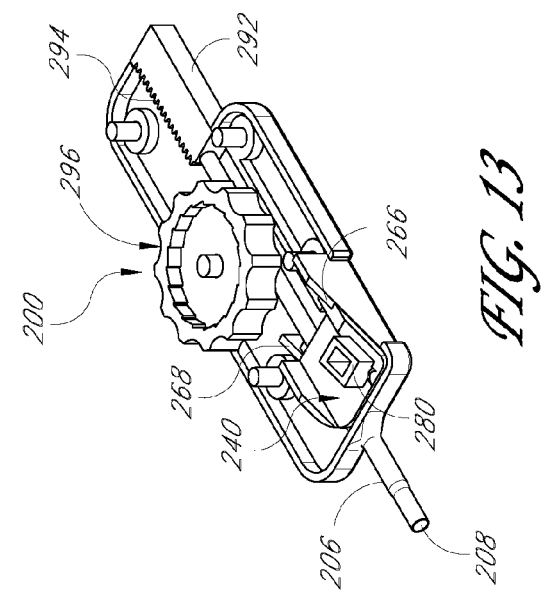
FIG. 14 is a perspective view of the apparatus of FIG. 3, with the upper housing portion removed for clarity, and the upper lens compactor moved to the second compacted position.
Figure 18:
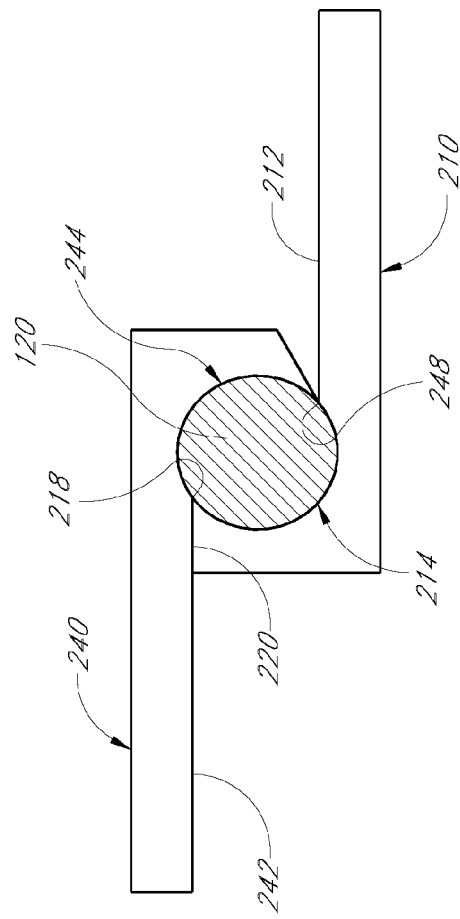
FIG. 18 a schematic, front cross-sectional view of the apparatus of FIG. 3, with the upper lens compactor in the second compacted position.

From the first compacted position, the upper lens compactor 240 may be advanced laterally to the second compacted position (see FIGS. 14, 18). As the upper lens compactor 240 is so advanced, the upper engagement face 242, inner surface 246 and/or upper insertion channel 244 urge the IOL 120 generally laterally toward the inner surface 216 and lower insertion channel 214. As best seen in FIG. 18, when the upper lens compactor 240 is in the second compacted position the upper insertion channel 244 is preferably disposed adjacent the lower insertion channel 214 such that they form a substantially complete cylinder which is substantially centered on the delivery axis A-A and forms a rearward extension of the delivery lumen 208. Accordingly, the inner surfaces 216, 246 and insertion channels 214, 244 "crush" the IOL 120 into a second compacted condition shown in FIG. 18.

With further reference to FIGS. 3-5 and 9-10, the apparatus 200 preferably further comprises a generally cylindrical driving member 290 which is disposed along the delivery axis A-A. (Where the delivery lumen 208 has an oval cross-section, the driving member 290 may have a similarly oval cross-section). The rearward end of the driving member 290 is connected to a rack 292 which forms rack teeth 294 on one side thereof. A pinion wheel 296 is rotatably mounted on a pinion wheel bearing 298 which projects upward from the lower housing 204. The pinion wheel 296, shown in further detail in FIGS. 19-20, forms on its underside a pinion gear 300 comprising pinion teeth 302 which are configured to mesh with the rack teeth 294, upon manual advancement of the rack 292 and driving member 290 forward from a storage position (shown in FIGS. 4, 13-14) to a ready position (not shown) in which the forwardmost rack teeth 294 engage the pinion teeth 302. Once the rack 294 and driving member 290 reach the ready position, the user may manipulate the pinion wheel 296 via knurling 304 formed on the outer surface thereof, to advance the rack 294 and driving member longitudinally forward in the apparatus 200. As this is done, ratchet cogs 306 formed on an inner surface of the pinion wheel 296 cooperate with a ratchet pawl 308 formed on the upper housing 202 to prevent counter-rotation of the pinion wheel 296 or rearward motion of the rack 294 and driving member 290.

Where the IOL 120 has been compacted into the second compacted configuration (or is otherwise disposed in the lower insertion channel 214 or between the insertion channels 214, 244 when the upper lens compactor 240 is in the second compacted position), this forward movement of the driving member 290 causes the forward end of the driving member to advance through the lower insertion channel (or between the insertion channels 214, 244 when the upper lens compactor 240 is in the second compacted position), thereby urging the IOL 120 forward and into the delivery lumen 208 of the delivery probe 206. Further advancement of the driving member will then extrude the IOL from the forward end of the delivery probe 206.

Except where otherwise noted, the components of the apparatus 200 may be formed from any suitably rigid material, including plastics such as ABS. The lower housing 204 (or, alternatively, at least the lower lens compactor 210 and/or delivery probe 206) may be formed from a transparent plastic such as clear polycarbonate, to promote visibility of the IOL during compaction/delivery.

Accordingly, the apparatus 200 may be employed to deliver or insert an IOL, such as the IOL 120, into an eye, such as a human eye. In doing so, the user/physician first accesses an insertion location (e.g., the capsular bag, anterior chamber, etc) within the eye via any suitable technique, for example, by making a small incision or series of small incisions in the anterior structures of the eye. If necessary, the natural crystalline lens is removed via a suitable technique such as phacoemulsification. Through the incision(s) the physician inserts the forward end of the delivery probe 206, preferably after compacting the IOL as detailed above and, if desired, after advancing the IOL partway through the lumen 208 of the delivery probe 206. With the end of the delivery probe in place, the physician extrudes the IOL from the probe 206, thereby inserting the IOL in the eye. (By employing the apparatus 200, the compacting and delivery may be done without opening the housing 202/204 or otherwise manually accessing the IOL). Upon departure from the probe 206, the IOL "un-compacts" by virtue of its elasticity, returning substantially to its unstressed condition. The physician then withdraws the probe 206 and, if necessary, adjusts the positioning of the IOL within the eye. Upon satisfactory positioning of the IOL, the physician closes the incision(s) to complete the operation.

FIGS. 21-29 depict another embodiment of an apparatus 400 for compacting and/or inserting an intraocular lens. In one embodiment, the apparatus 400 is generally similar to the apparatus 200 described above and depicted in FIGS. 3-20, except as further detailed below. Except where otherwise noted, the components of the apparatus 400 may be formed from any suitably rigid material, including plastics such as ABS.

The apparatus 400 preferably comprises an upper housing 402 and a lower housing 404 which cooperate to enclose and support the components of the apparatus 400. Disposed within the lower housing 404 is an injector plate 405 which forms a delivery probe 406 which in turn defines a delivery lumen 408; both the delivery probe 406 and lumen 408 extend along a longitudinally-oriented delivery or injection axis A-A of the apparatus 400. The injector plate 405 also forms a lower lens compactor or lower compacting element 410 comprising a lower engagement face or wall 412 and a lower insertion channel 414 which extends along the delivery axis A-A.

Figure 24:
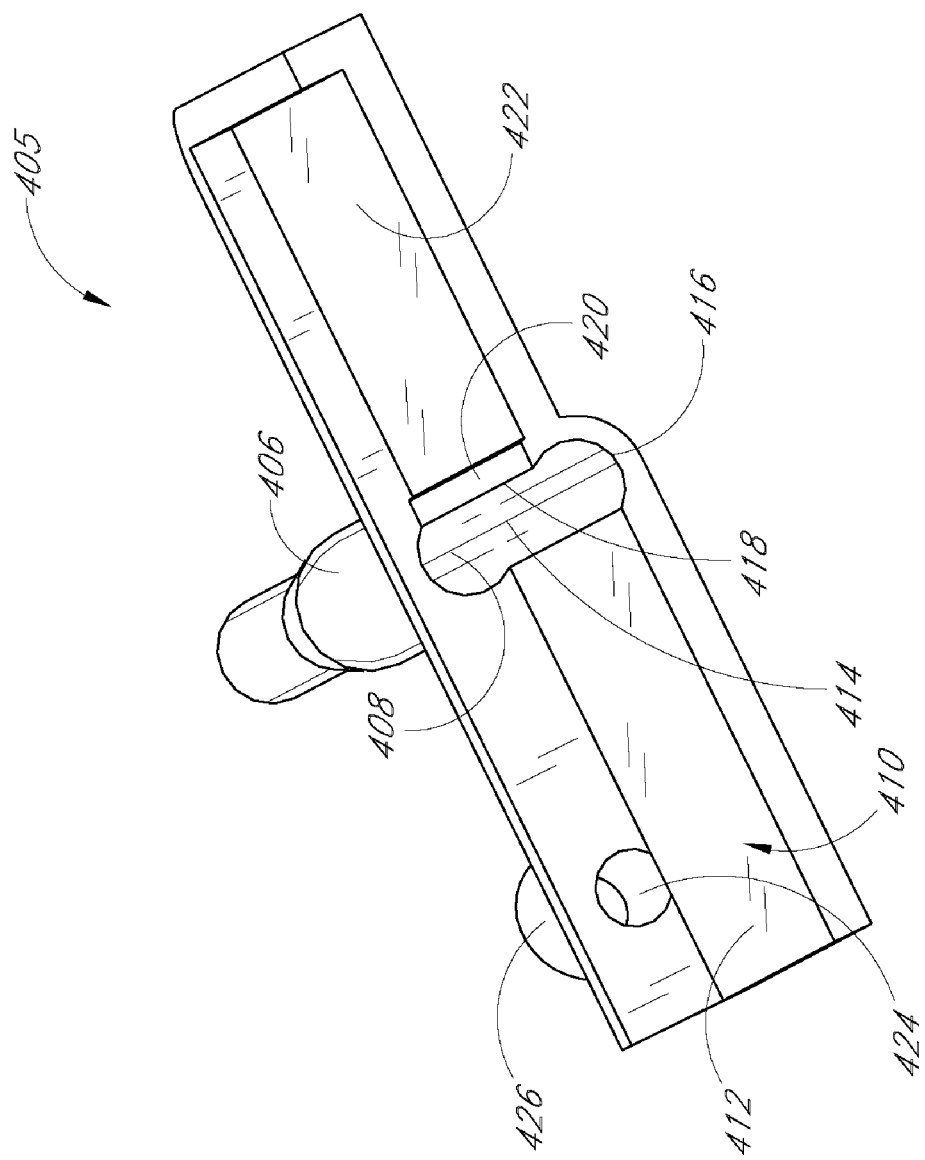
FIG. 24 is a perspective view of the injector plate of the apparatus of FIG. 21.

Best seen in FIG. 24, the lower engagement face 412 preferably comprises a generally flat surface which defines a plane extending generally parallel to (or intercepting) the delivery axis A-A. The lower insertion channel 414 is preferably a partial cylinder in shape, with an inner surface 416 which extends from the lower engagement face 412 to a lower channel edge 418 which preferably extends generally parallel to the delivery axis A-A. The lower insertion channel 414 preferably comprises a partial rearward extension, along the delivery axis A-A, of the inner surface of the delivery lumen 408. From the lower channel edge 418 a lower support surface 420 extends in a direction opposite the lower engagement face 412, while forming a generally flat surface which defines a plane extending generally parallel to the face 412. In the depicted embodiment, the lower support surface is slightly elevated with respect to a lower lateral surface 422 extending from the lower support surface 420 opposite the lower insertion channel 414. If desired, a lubricant opening 424 and lubricant fitting 426 may be provided in fluid communication with the lower lens compactor 410 to facilitate lubrication of the IOL during compaction.

The opening 424 also facilitates visibility of the IOL within the apparatus 400 at various stages of the compaction/delivery process. To further promote visibility of the IOL during compaction/delivery, a window or opening 407 may be formed in the lower housing 404 (see FIGS. 21-22, 28), and the lower engagement face 412 (or the entire injector plate 405) may be formed from a transparent material. Where the entire injector plate 405 is constructed from a transparent material, the post-compaction condition of the IOL will be visible in the delivery probe 406.

Referring again to FIGS. 21-22 and also to FIGS. 25-26, an upper lens compactor 440 is slidably disposed generally above the lower lens compactor 410. The lower and upper lens compactors 410, 440 together form a lens compactor of the apparatus 400. The upper lens compactor 440 forms an upper engagement face 442 which preferably comprises a generally flat surface which, when the upper lens compactor is in position on the lower housing 404, defines a plane extending generally parallel to the delivery axis A-A. The upper lens compactor 440 preferably further comprises an upper insertion channel 444, which is preferably a partial cylinder in shape, with an inner surface 446 which extends from the upper engagement face 442 to an upper channel edge 448 which preferably extends generally parallel to the delivery axis A-A. (Alternatively, the insertion channels 414, 444 may taper inward as they extend forward, thereby forming a truncated cone or another inward-tapering surface upon their convergence when the upper lens compactor 440 is in the second compacted position (see below). Instead of or in addition to such a configuration of the insertion channels 414, 444, the inner surface of the delivery lumen 408 may also taper inward as it extends forward).

In yet another embodiment, the delivery lumen 408 can have a generally oval cross-section (taken orthogonal to the delivery axis), with the channels 414, 444 shaped to have a similarly oval cross-section upon their convergence when the upper lens compactor 440 is in the second compacted position (see below).

The upper lens compactor 440 preferably further comprises first and second upper bearing surfaces 460, 462 disposed on respective opposite sides of the upper engagement face 442 and upper insertion channel 444. The first and second upper bearing surfaces 460, 462 preferably comprise generally flat surfaces which extend longitudinally and are sloped with respect to the upper engagement face 442 and/or delivery axis A-A. The first and second upper bearing surfaces 460, 462 are (at least initially) slidably disposed against similarly-sloped first and second lower bearing surfaces 466, 468 formed on support ribs 470, 472 of the lower housing 404 (see FIG. 29). The upper lens compactor 440 further comprises an interface slot 450 which mates with an interface tab 452 formed on a compactor actuator 480.

Figure 28:
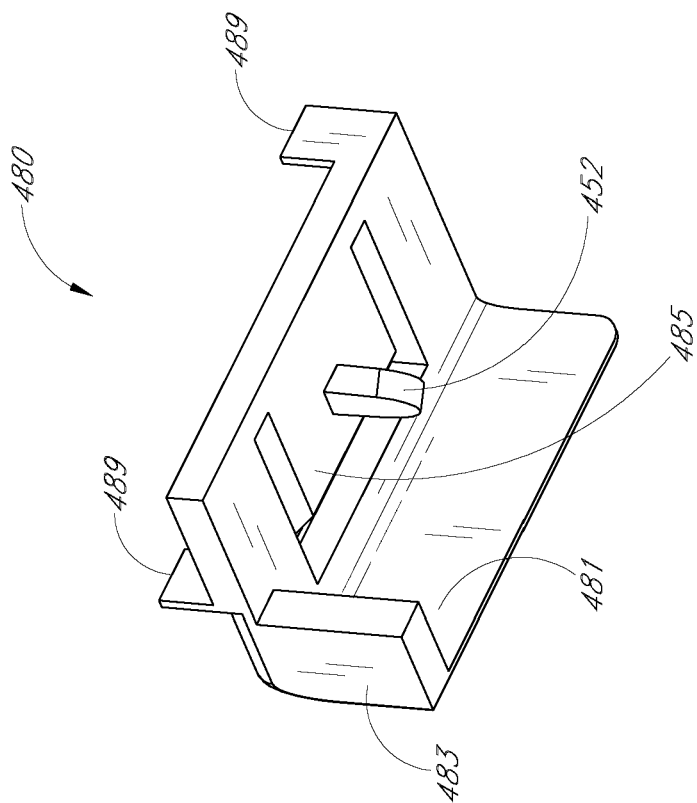
FIG. 28 is a second perspective view of the compactor actuator of the apparatus of FIG. 21.
Figure 27:
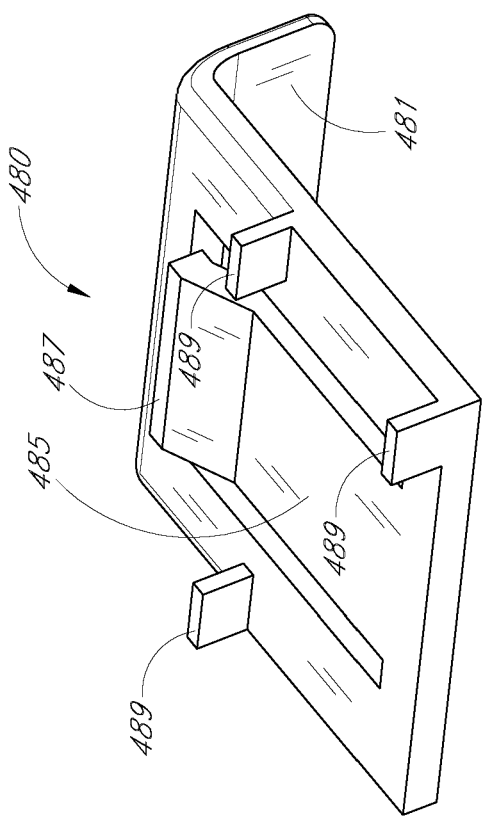
FIG. 27 is a perspective view of the compactor actuator of the apparatus of FIG. 21.
Figure 29:
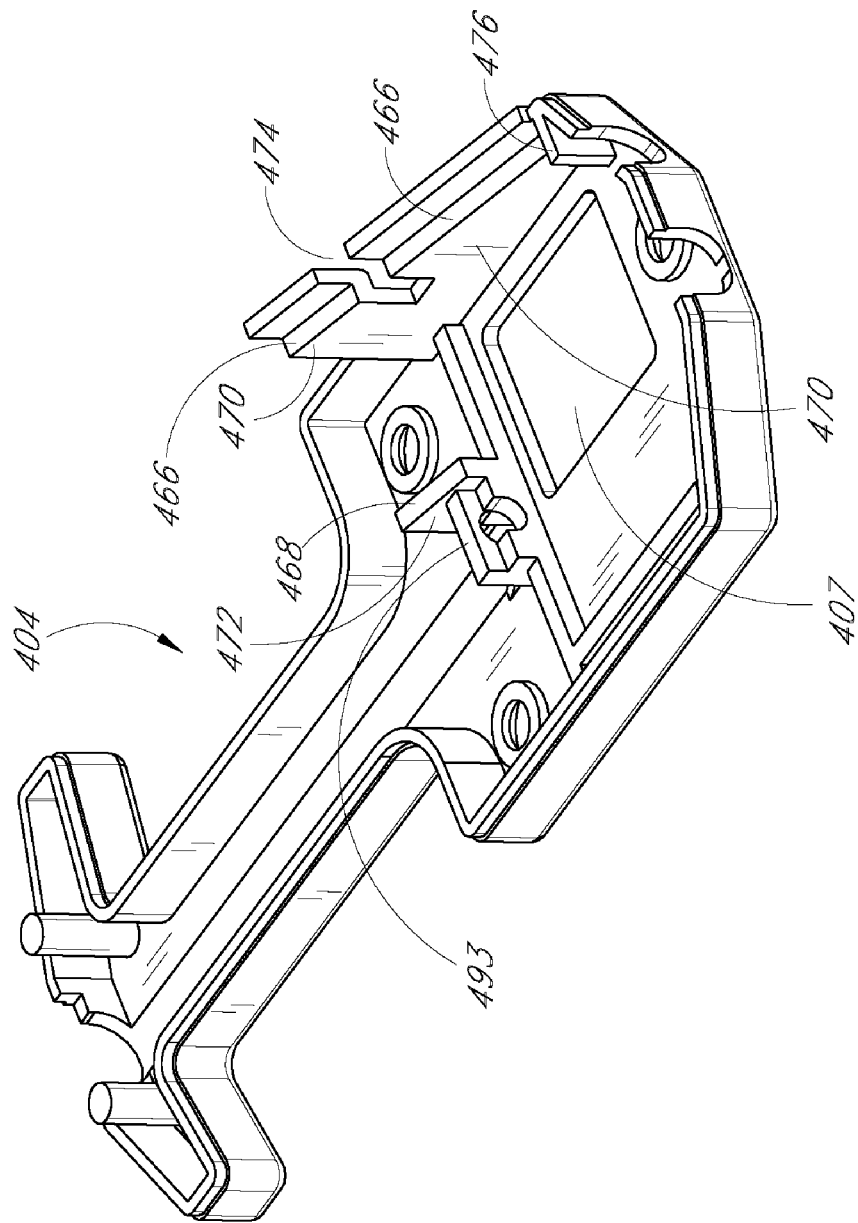
FIG. 29 is a perspective view of the lower housing of the apparatus of FIG. 21.

FIGS. 27-28 depict a preferred configuration of the compactor actuator 480. The actuator 480 preferably comprises a unitary member having a generally longitudinal handle 481 and a generally lateral guide rib 483. A spring member 485 extends laterally across an opening formed in the upper surface of the compactor actuator 480, and forms a spring tab 487 on its free end. Extending generally upward from the upper surface of the compactor actuator 480 are a number of guide projections 489, the upper ends of which are disposed within corresponding compactor guides 482 (see FIG. 22) formed on the inward upper surface of the upper housing 402. In the depicted embodiment, each of the compactor guides 482 comprises a generally longitudinal slot 484 and a generally lateral slot 486 which are joined in an "L" configuration. The lateral slot(s) 486 may extend purely laterally, or (in the depicted embodiment) they may be angled slightly forward, forming an angle of slightly more than 90 degrees with the corresponding longitudinal slot(s) 484.

Thus, the compactor actuator 480 is employed to move and guide the upper lens compactor 440 along a range of motion (similar to that of the upper lens compactor 240 of the apparatus 200) between a home position, first compacted position and second compacted position. At the home position, the upper lens compactor 440 is rearwardly disposed on the ribs 470, 472, with the first upper bearing surface 460 resting on the first lower bearing surface 466 and straddling a gap 474 formed in the surface 466/rib 470, and with the second upper bearing surface 462 resting on the second lower bearing surface 468. In one embodiment, the rearward edges of the surfaces 460 and 466 (and/or those of the surfaces 462 and 468) are aligned when the upper lens compactor 440 is in the home position.

From the home position, the actuator 480 and compactor 440 can be moved longitudinally forward by appropriate manipulation of the handle 481, to the first compacted position in which the first upper bearing surface 460 may remain on the first lower bearing surface 466, but forward of the gap 474, and the second upper bearing surface 462 is displaced forward of, and no longer rests on, the second lower bearing surface 468. In addition, the lateral guide rib 483 is longitudinally aligned with or forward of the gap 474, thereby permitting (subsequent) inward lateral movement of the actuator 480 and compactor 440, and the guide projections 489 are disposed at the forward ends of the longitudinal slots 484 of the corresponding compactor guides 482 (see FIG. 22). The first compacted position is, in one embodiment, further characterized by relative situation of the compactors 410, 440, bearing faces 412, 442, channels 414, 444, edges 418, 448, etc. in a manner similar to that depicted in FIGS. 16-17 with regard to the apparatus 200. In another embodiment, the first compacted position is still further characterized by contact between a forward edge of the upper lens compactor 440 and a stop member 476 formed on the lower housing 404.

From the first compacted position, the actuator 480 and compactor 440 can be moved generally laterally inward to the second compacted position. The second compacted position is, in one embodiment, characterized by relative situation of the compactors 410, 440, bearing faces 412, 442, channels 414, 444, edges 418, 448, etc. similar to that depicted in FIG. 18 with regard to the apparatus 200. As the compactor 440 and actuator 480 advance laterally inward, their motion is guided by the interaction of the guide projections 489 and the lateral slots 486 of the corresponding compactor guides 482, until the second compacted position is reached. In addition, the lateral guide rib 483 moves laterally into the housings 402, 404 through the gap 474. In one embodiment, the spring member 485 and spring tab 487 of the actuator 480 move sufficiently laterally inward to cause the outer edge of the tab 487 to engage the inner edge of a locking ridge 488 (see FIG. 22) formed on the upper housing 402. The spring member 485 prevents disengagement of the tab 487 and ridge 488, thereby preventing backward/outward lateral movement of the actuator 480 and upper lens compactor 440, once the second compacted position has been reached. This in turn ensures the creation of a rigid, stable "cylinder" at the meeting of the upper and lower insertion channels 414, 444 in the second compacted position, and a smooth longitudinal advancement of the compacted IOL from the "cylinder" into the delivery probe 406. Where employed, the spring member 485, tab 487 and ridge 488 also cooperate to make the apparatus 400 a single-use device, ensuring that factory-controlled standards for sterility, suitability of IOL type, etc. may be enforced with respect to each use of an apparatus 400.

Figure 21:
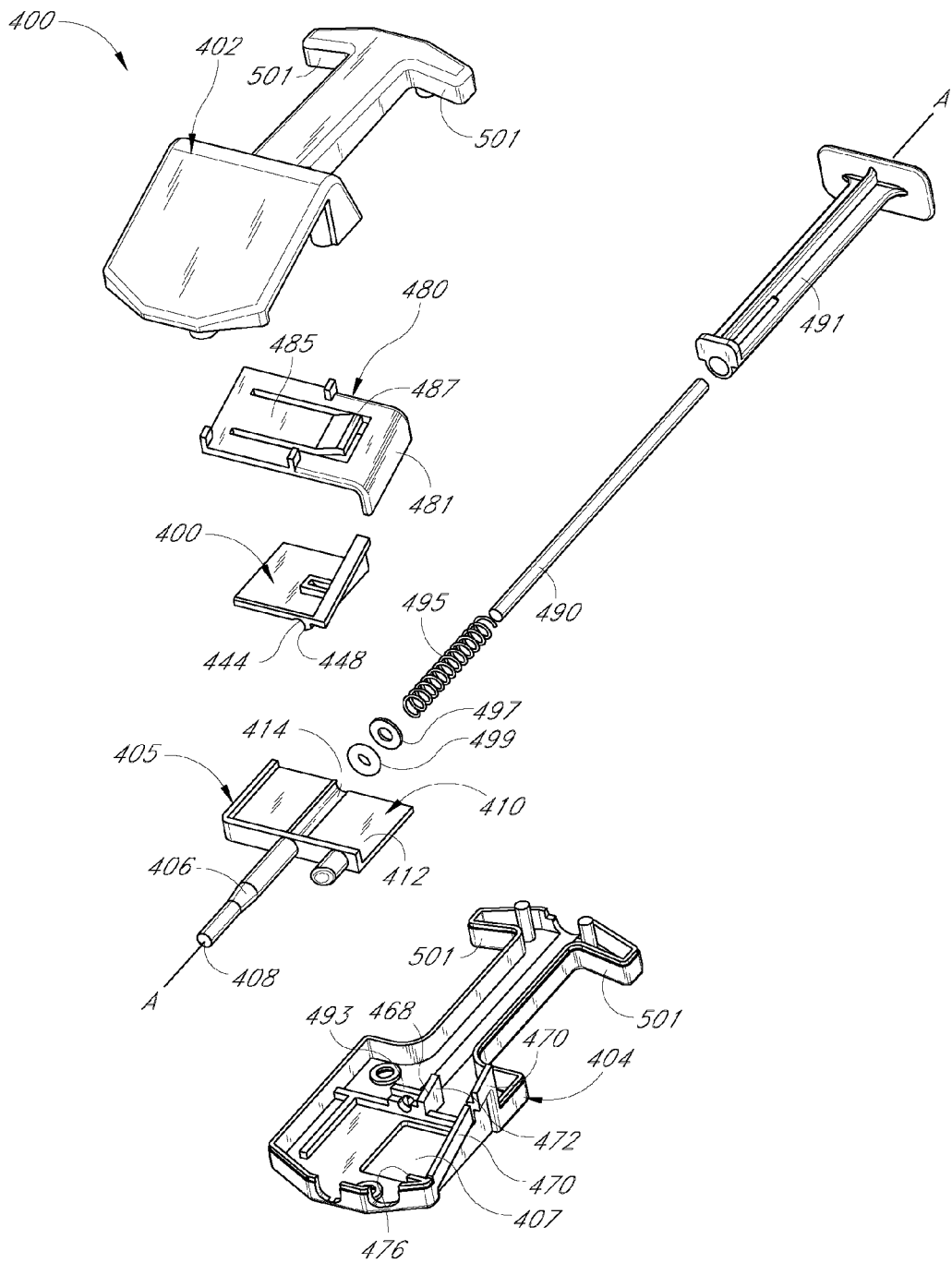
FIG. 21 is an exploded view of a second embodiment of an apparatus for compacting and/or inserting an intraocular lens.
Figure 22:
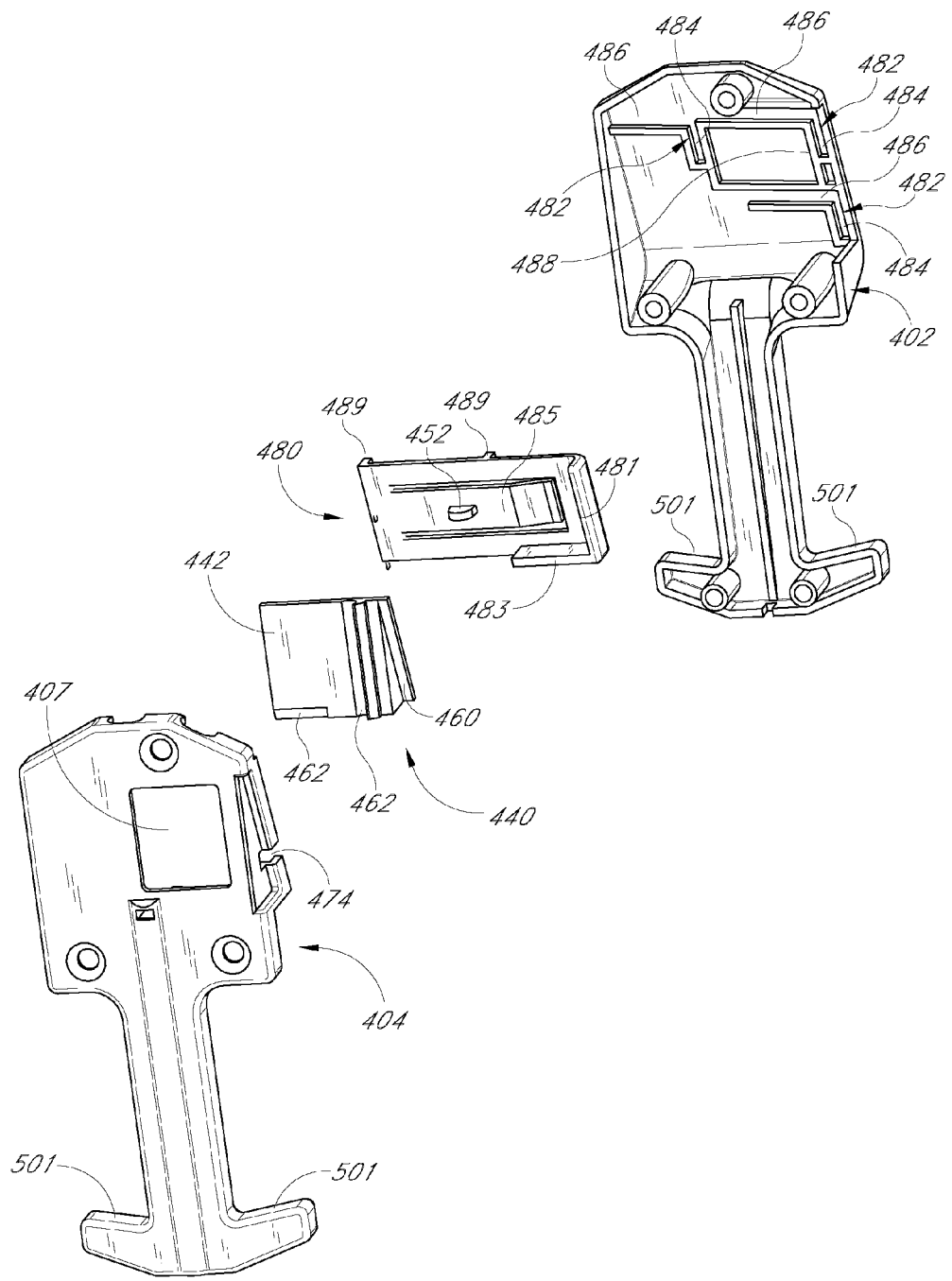
FIG. 22 is a second, partial exploded view of the apparatus of FIG. 21.
Figure 23:
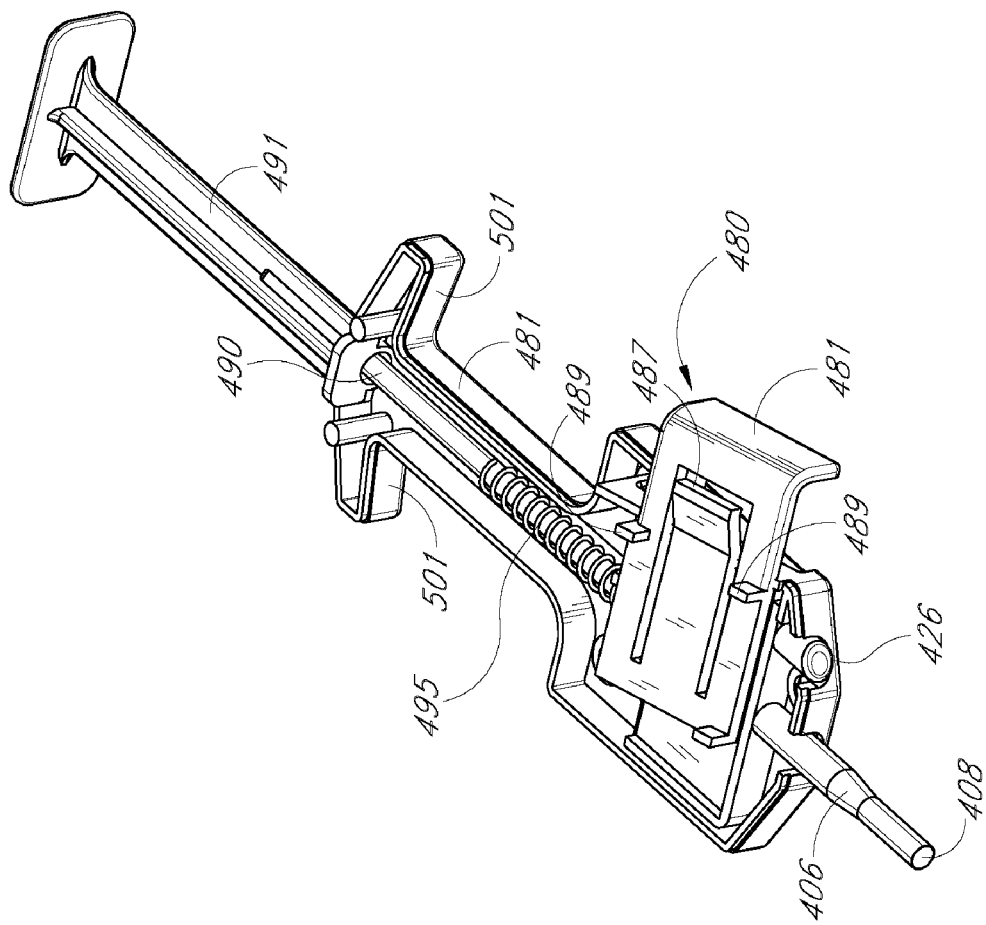
FIG. 23 is a perspective view of the apparatus of FIG. 21, with the upper housing removed for clarity.

With further reference to FIGS. 21-22, the apparatus 400 further comprises a generally cylindrical driving member 490 which is disposed along the delivery axis A-A. (Where the delivery lumen 408 has an oval cross-section, the driving member 490 may have a similarly oval cross-section). The rearward end of the driving member 490 is received in a plunger 491 which is slidably disposed between the upper and lower housings 402, 404. The lower housing 404 forms a driving member guide 493 situated on the delivery axis A-A. Via appropriate manipulation of the plunger 491, the driving member 490 is longitudinally moveable from a retracted position (shown in FIG. 23), in which the forward end of the driving member 490 is situated in the driving member guide 493, forward through the lower insertion channel 414 (or between the insertion channels 414, 444 when the upper lens compactor 440 is in the second compacted position), thereby urging the IOL 120 forward and into the delivery lumen 408 of the delivery probe 406. Further advancement of the driving member will then extrude the IOL from the forward end of the delivery probe 406.

A spring 495, washer 497 and O-ring 499 may be situated surrounding the driving member 490 between the driving member guide 493 and the plunger 491. In addition, finger grips 501 may be provided on the upper and/or lower housings 402, 404 to facilitate holding the apparatus 400 between the thumb and forefingers, in a "syringe" fashion, with the thumb on the rear of the plunger 491 and one forefinger on each of the finger grips 501. This arrangement likewise facilitates single-handed operation of the apparatus 400 when delivering/inserting an IOL situated in the lower insertion channel 414. The spring 495 provides resistance and tactile feedback when a user is urging the driving member 490 forward with the plunger 491; if desired, the spring 495 and plunger 491 may be sized to reach an abutting relation (and thereby provide this resistance/feedback) once the forward end of the plunger 491 has entered the delivery lumen 408.

Accordingly, the apparatus 400 may be employed to deliver or insert an IOL, such as the IOL 120, into an eye, such as a human eye. In doing so, the user/physician first accesses an insertion location (e.g., the capsular bag, anterior chamber, etc) within the eye via any suitable technique, for example, by making a small incision or series of small incisions in the anterior structures of the eye. If necessary, the natural crystalline lens is removed via a suitable technique such as phacoemulsification. Through the incision(s) the physician inserts the forward end of the delivery probe 406, preferably after compacting the IOL as detailed above and, if desired, after advancing the IOL partway through the lumen 408 of the delivery probe 406. With the end of the delivery probe in place, the physician extrudes the IOL from the probe 406, thereby inserting the IOL in the eye. (By employing the apparatus 400, the compacting and delivery/insertion may be done without opening the housing 402/404 or otherwise manually accessing the IOL). Upon departure from the probe 406, the IOL "un-compacts" by virtue of its elasticity, returning substantially to its unstressed condition. The physician then withdraws the probe 406 and, if necessary, adjusts the positioning of the IOL within the eye. Upon satisfactory positioning of the IOL, the physician closes the incision(s) to complete the operation.

Figure 30:
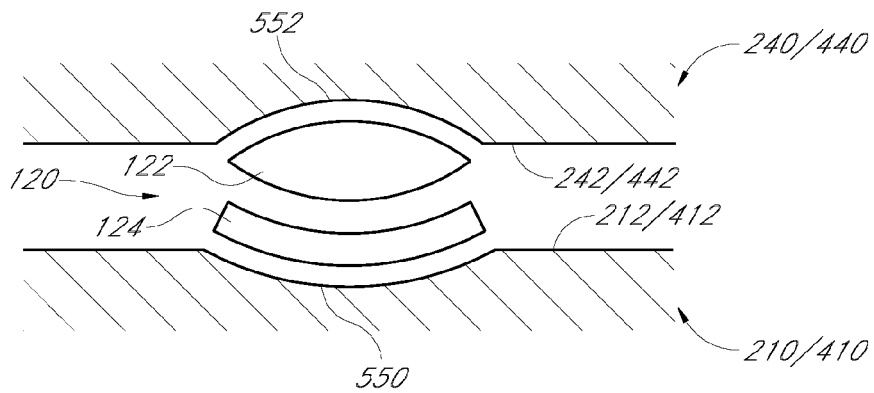
FIG. 30 is a schematic, cross-sectional view of alternative engagement faces for use with the disclosed apparatus.
Figure 31:
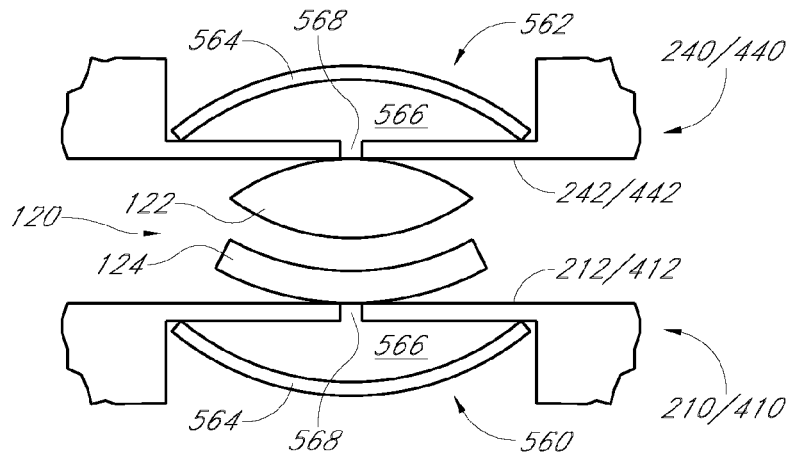
FIG. 31 is a schematic, cross-sectional view of vacuum-type engagement faces for use with the disclosed apparatus.
Figure 32:
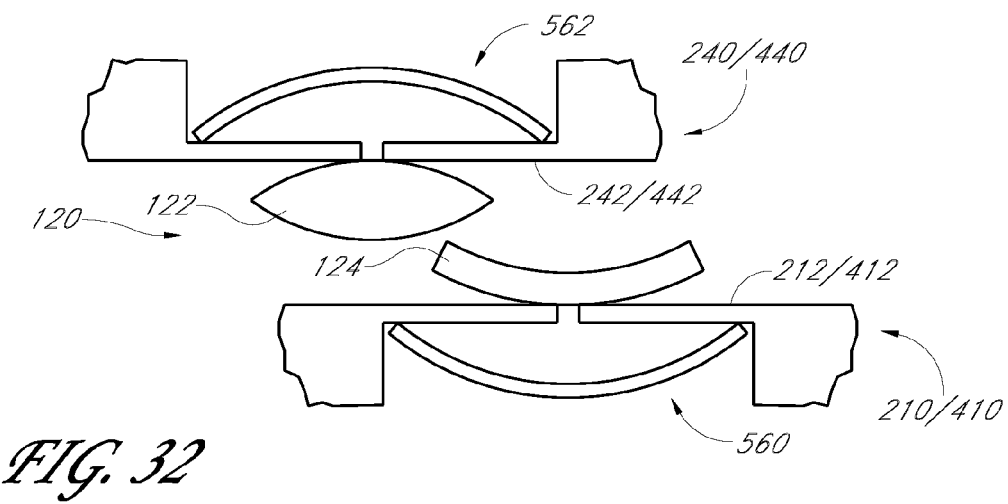
FIG. 32 is a schematic, cross-sectional view of vacuum-type engagement faces for use with the disclosed apparatus, with the upper lens compactor in the first compacted position.

FIGS. 30-32 depict alternative structures that may be employed in connection with one or both of the lower and upper engagement faces 212/412, 242/442, instead of or in addition to the generally flat surfaces described above. For example, FIG. 31 depicts the use of one or more pockets 550, 552 formed in the faces 212/412, 242/442. The pockets 550, 552 may be suitably shaped (e.g. as partial, substantially cylindrical or spherical shells, or with a rectangular or other polygonal profile) to grip the respective viewing elements 124, 122. In a further embodiment, the pocket(s) 550, 552 may be formed from a material, such as any of the materials discussed above, having an adhesive affinity for the material(s) employed to construct the outer faces of the viewing elements.

As seen in FIGS. 31-32, vacuum grips 560, 562 may be employed in connection with the engagement face(s) 212/412, 242/442. In the depicted embodiment, each vacuum grip 560, 562 comprises a domelike button 564 enclosing a vacuum chamber 566 in fluid communication with a relief opening 568 formed in the respective engagement face(s) 212/412, 242/442 which is positioned to abut the respective viewing element(s) 124, 122. Thus, depression of the button(s) 564 expels air from the relief openings 568, and the resilient properties of the button(s) 564 are sufficient to urge the button(s) 564 toward their original position. The negative pressure thereby created in the vacuum chamber(s) 566 draws the viewing element(s) 124, 122 against the engagement face(s) 212/412, 242/442. With the viewing elements so gripped, the compactors 210/410, 240/440 may be relatively moved to place the IOL 120 in the first compacted configuration shown in FIG. 32.

As yet another alternative, one or both of the engagement face 212/412, 242/442 may be suitably roughened to engage the viewing elements 122, 124. Such surface roughening may be employed on its own, or in connection with any of the alternatives discussed herein for constructing the engagement face 212/412, 242/442. In one embodiment, the surfaces in question are sanded; as one example, 100 grit sandpaper may be employed. In other embodiments, the surfaces may be ribbed, knurled, etc.

In further embodiments of the apparatus 200/400, the lower housing 204/404, lower lens compactor 210/410 and/or upper lens compactor 240/440 may be configured such that the upper lens compactor 210/410 is moveable only from the first compacted position to the second compacted position. In other words, the first compacted position replaces the home position as the "start" location of the upper lens compactor 240/440, which can move from the first compacted position to the second compacted position in the manner already described. Any or all of the structures described above as facilitating longitudinal movement of the upper lens compactor 210 between the home and first compacted positions may be omitted, if desired. The balance of the structure and function of the apparatus 200/400 preferably remains as described above.

Such a modified apparatus 200/400 is particularly useful for compacting and/or inserting a single-lens IOL, such as (but not limited to) the IOL 100 described above. Alternatively, a multiple-lens IOL, such as (but not limited to) the IOL 120 described above, may be compacted and/or inserted with this modified apparatus. In one embodiment, the multiple-lens IOL is disposed or stored in the compactor in the first compacted condition described above, when the upper lens compactor is in the first compacted position (again, the "start" location of the upper lens compactor). In another embodiment, the multiple-lens IOL is disposed or stored in the compactor in the substantially unstressed condition described above, when the upper lens compactor is in the first compacted position.

As described above, FIGS. 15-18 illustrate schematically the operation of embodiments of lens compactors in a circumstance in which a multiple-lens IOL, such as the IOL 120 described above, is stored or placed in the apparatus 200/400 for subsequent compaction and/or insertion into the eye of a patient. As shown in FIG. 15, the multiple-lens IOL 120 is disposed within the apparatus 200/400 in a substantially unstressed condition (or "home" condition) in which the optical axes of the viewing elements are substantially coincident with each other, and/or with the optical axis of the IOL 120 itself. In certain embodiments, the IOL 120 is compacted by, for example, first advancing the compactor actuator 280/480 generally longitudinally from a home position to a first compacted position in which the viewing elements are relatively displaced (see FIGS. 16 and 17). The compactor actuator 280/480 then is advanced generally laterally so as to "crush" the IOL 120 into a second compacted configuration (see FIG. 18) for subsequent delivery/insertion through the delivery probe 206/406 along the generally longitudinally oriented delivery or injection axis A-A (see FIGS. 5 and 21).

In certain embodiments, the IOL 120 is stored within the lens compactor in an initial orientation (or initial configuration) that provides for easier compaction and/or delivery of the IOL 120. For example, in certain embodiments, the initial orientation of the IOL 120 is selected to facilitate the relative displacement of the individual viewing elements of the IOL 120 when the apparatus 200/400 is changed from the home position to the first compacted position. The initial IOL orientation that provides for improved compaction/delivery will generally depend on the characteristics of the apparatus 200/400 (e.g., the shape and configuration of the lens compactors, engagement surfaces, etc.) as well as on the characteristics of the IOL 120 (e.g., the shape and configuration of the viewing elements, biasing members, and other IOL features). Additionally, a suitable initial IOL orientation may depend on the direction(s) along which compaction forces are applied by the apparatus 200/400 and on the desired direction of relative displacement of the viewing elements with respect to the delivery axis A-A. Embodiments of the apparatus 200/400 in which the IOL 120 can be stored with such an initial orientation advantageously provide not only easier compaction and delivery of the IOL but also a reduced likelihood of tearing or damaging the IOL during the compaction/delivery process.

Figure 33:
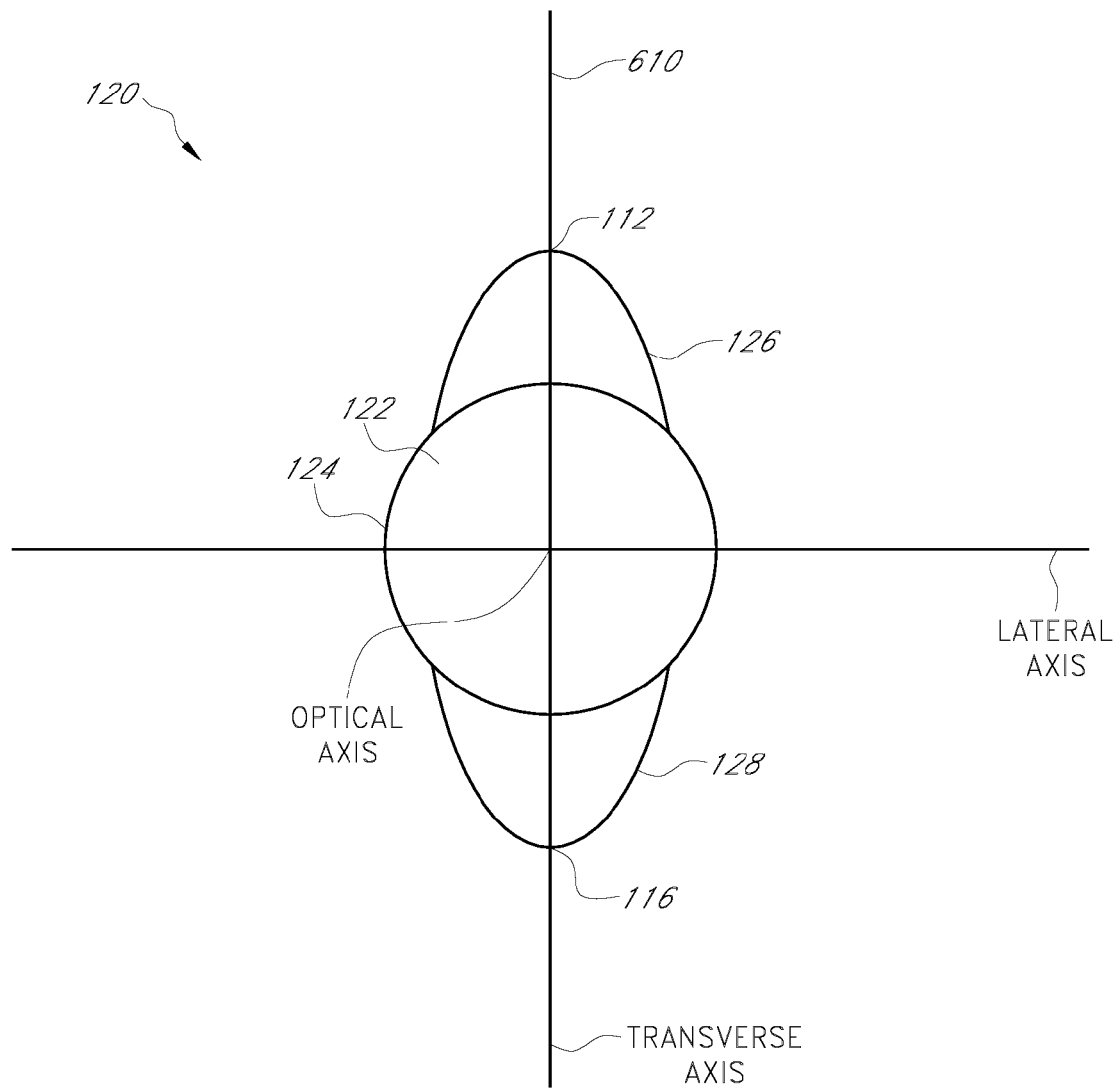
FIG. 33 is a schematic front view of an embodiment of a multiple-lens IOL having a longitudinal bisection axis.
Figure 34:
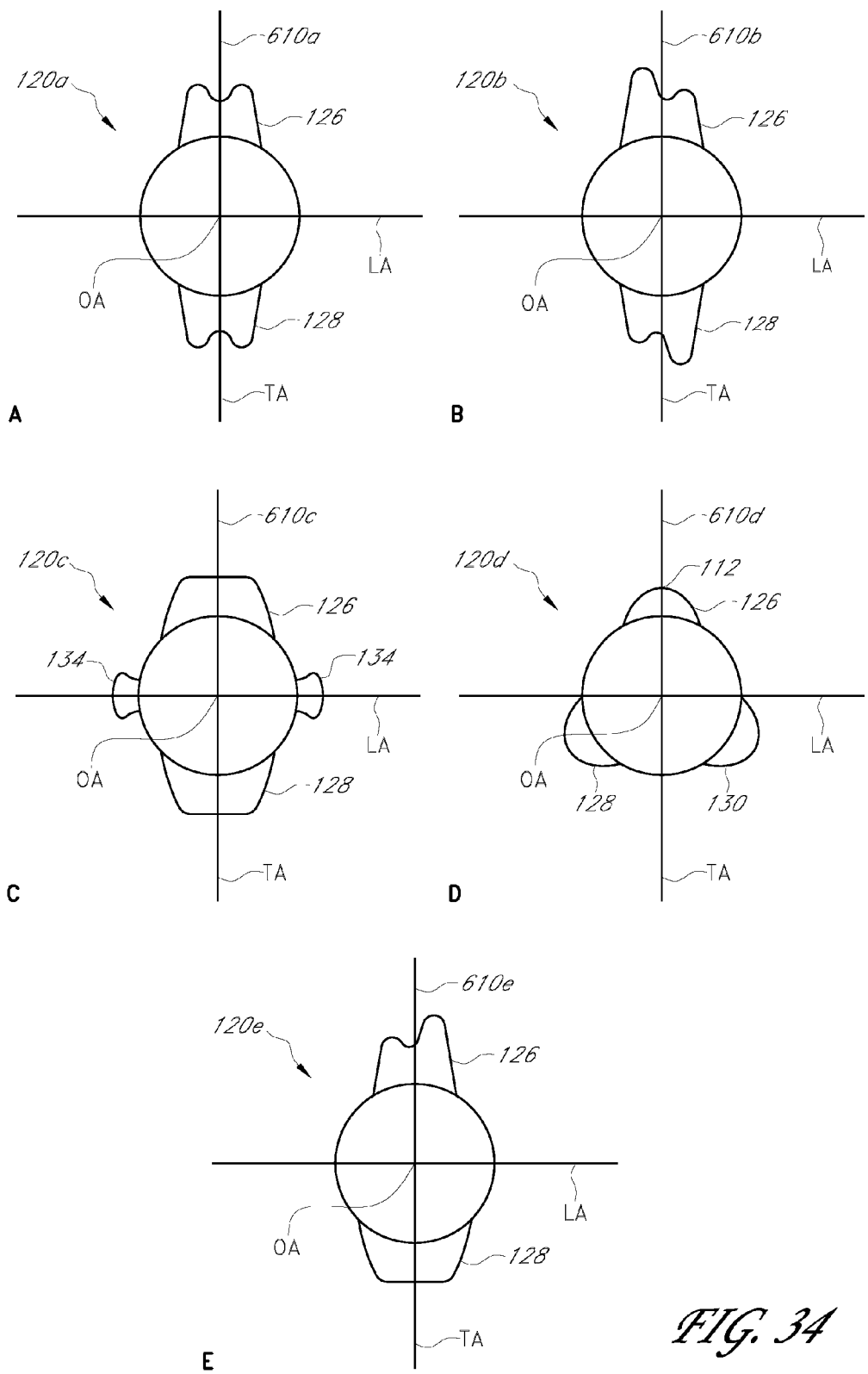
FIGS. 34A-34E are schematic front views of other embodiments of multiple-lens IOLs, with each IOL having a longitudinal bisection axis.

FIG. 33 is a front view that schematically illustrates an embodiment of a dual- or multiple-lens IOL 120. Some embodiments of the IOL 120 are generally similar to the IOL illustrated in FIG. 2. The IOL 120 shown in FIG. 33 comprises first and second viewing elements 122, 124 and biasing members 126, 128 which join the first and the second viewing elements 122, 124. The IOL 120 has an optical axis that is substantially coincident with the optical axes of the viewing elements 122 and 124. As shown in FIG. 33, the optical axis is depicted as a point at the center of the viewing elements 122, 124, and the optical axis extends substantially perpendicularly with respect to the plane of FIG. 33. As described above, a lateral axis and a transverse axis may be defined substantially perpendicularly to the optical axis. In the configuration shown in FIG. 33, the lateral axis extends in a generally horizontal (or left-right) direction, and the transverse axis extends in a generally vertical (or up-down) direction.

The IOL 120 generally is disposed within the apparatus 200/400 for insertion/delivery into an eye of a patient. In order to describe an initial orientation of the IOL 120 within the apparatus 200/400, it is useful to define a longitudinal bisection axis 610 of the IOL 120, which indicates a characteristic or reference direction of the IOL 120 itself. For any particular IOL configuration, the longitudinal bisection axis 610 can be determined as described below. The initial orientation of the IOL 120 within the apparatus 200/400 may be conveniently determined by identifying an initial orientation angle between the longitudinal bisection axis 610 of the IOL 120 and some other suitable characteristic or reference direction within the apparatus 200/400. The initial orientation angle preferably is determined while the IOL 120 is in the home condition, prior to any compaction processes.

The longitudinal bisection axis 610 of the IOL 120 preferably is selected to indicate a generally longitudinal direction of the IOL 120 within a plane substantially perpendicular to the optical axis. As shown in FIG. 33, the longitudinal bisection axis 610 lies in the plane defined by the lateral and transverse axes of the IOL 120. Some embodiments of the IOL 120 may have a cross-sectional shape that is substantially symmetrical with respect to one (or more) directions defined in the plane of the transverse and lateral axes. In such embodiments, the longitudinal bisection axis 610 is selected to coincide with a direction of symmetry of the IOL 120. If the IOL 120 has more than one symmetry axis, the longitudinal bisection axis 610 is selected as the symmetry axis along which the overall length of the IOL is greatest (e.g., a generally longitudinal axis).

For example, in certain embodiments the IOL 120 has reflection symmetry (also called mirror symmetry or bilateral symmetry) such that if the cross-sectional shape of the IOL were folded in half across the symmetry axis, the two halves would have substantially the same shape. As illustrated in FIG. 33, the IOL 120 is substantially mirror symmetrical about both the transverse axis and the lateral axis. In this embodiment, the longitudinal bisection axis 610 is selected to coincide with the transverse axis, because the IOL 120 has its greatest length along this axis. Accordingly, as shown in FIG. 33, the longitudinal bisection axis 610 extends along a line that intersects the IOL 120 at an upper apex 112 of the biasing member 126, passes through the optical axis, and intersects a lower apex 116 of the biasing member 128.

Although the longitudinal bisection axis 610 of the IOL 120 shown in FIG. 33 coincides with the transverse axis, this is not a requirement. In other embodiments, depending on the cross-sectional configuration of the IOL 120, the longitudinal bisection axis 610 may coincide with the lateral axis or with any other suitable axis that is generally perpendicular to the optical axis (OA). For example, the longitudinal bisection axis 610 may be selected to be a direction of symmetry of the IOL or may be selected to correspond to a generally longitudinal direction in the IOL. After the longitudinal bisection axis 610 for any particular IOL 120 is defined (e.g., based on the particular cross-sectional shape of the IOL; see, e.g., FIGS. 34A-34E below), the longitudinal bisection axis 610 serves as a reference axis by which the initial orientation of the IOL 120 can be defined with respect to the apparatus 200/400.

FIGS. 34A-34E schematically illustrate front views of other embodiments of IOLs and show suitable selections for the orientation of the longitudinal bisection axis in each of these IOLs. For example, FIG. 34A illustrates an IOL 120a having biasing members 126, 128 that are shaped differently from the biasing members of the IOL 120 illustrated in FIG. 33. The IOL 120a has reflection symmetry with respect to both the transverse axis (TA) and lateral axis (LA). As with the IOL 120 shown in FIG. 33, the longitudinal bisection axis 610a of the IOL 120a is selected to coincide with the transverse axis, because the transverse axis corresponds to a greater length of the IOL 120a than does the lateral axis.

FIG. 34B illustrates an embodiment of an IOL 120b which does not have reflection symmetry with respect to either the transverse axis or the lateral axis. However, as can be seen from FIG. 34B, the transverse axis and the lateral axis each generally bisect the IOL 120b into two substantially congruent portions (e.g., portions having substantially the same shape and size but in different positions or orientations relative to each other). Accordingly, the transverse axis and the lateral axis are lines of bisection of the IOL 120. In this embodiment, the longitudinal bisection axis 610b is selected to coincide with the transverse bisection axis of the IOL 120b, because the length of the IOL 120b is larger along this axis than along the lateral axis.

FIG. 34C illustrates an IOL 120c that has distending portions 134 used to help anchor the IOL 120c in the eye of the patient. The transverse and lateral axes of the IOL 120c correspond to axes of reflection symmetry (as well as being lines of bisection), and as described above with reference to FIGS. 33 and 34A-34C, the longitudinal bisection axis 610c is selected to be the "longer" of these two axes, namely, the transverse axis.

FIG. 34D schematically illustrates a front view of an IOL 120d having three biasing members 126, 128, and 130 that are disposed substantially symmetrically around the optical axis. The IOL 120d has three axes of reflection symmetry (e.g., along lines passing through the optical axis and apexes of the biasing members). The longitudinal bisection axis 610d may be selected as any one these substantially equivalent symmetry axes, for example, along the direction passing through the optical axis and the apex 112 of the biasing member 126.

A longitudinal bisection axis may be defined for any IOL, including IOLs that do not possess, for example, an axis of reflection symmetry or a line of bisection. For example, FIG. 34E schematically illustrates a front view of an IOL 120e in which the biasing members 126, 128 are not symmetrically disposed about the viewing elements. In such embodiments, a longitudinal bisection axis 610e may be selected to coincide with a line passing through the optical axis and extending along a generally longitudinal direction of the IOL. In the embodiment shown in FIG. 34E, the longitudinal bisection axis 610e is selected to coincide with the transverse axis of the IOL 120e. In some embodiments, the longitudinal bisection axis 610 of an IOL may be selected to correspond to a preferred direction of the IOL when it is implanted within the patient's eye (e.g., a substantially vertical direction when the patient is upright).

The longitudinal bisection axis 610 of an IOL 120 can conveniently be used to define an initial orientation of the IOL 120 as packaged within the lens compactor prior to compaction/delivery into the eye. For example, in some embodiments, the initial orientation of the IOL 120 may be referenced by an angle (herein denoted by $\theta$) defined between the direction of the longitudinal bisection axis 610 of the IOL 120 and the direction of the delivery or injection axis A-A (see, e.g., FIGS. 3 and 21). In other embodiments, the initial orientation of the IOL 120 may be determined with reference to an angle defined between the longitudinal bisection axis 610 and the direction of some other suitable portion of the apparatus 200/400. In yet other embodiments, the initial orientation of the IOL 120 may be defined with reference to a suitable direction within the apparatus 200/400 (e.g., the direction in which the upper engagement face 242/442 advances from the home to the first compacted position).

Figure 35A:
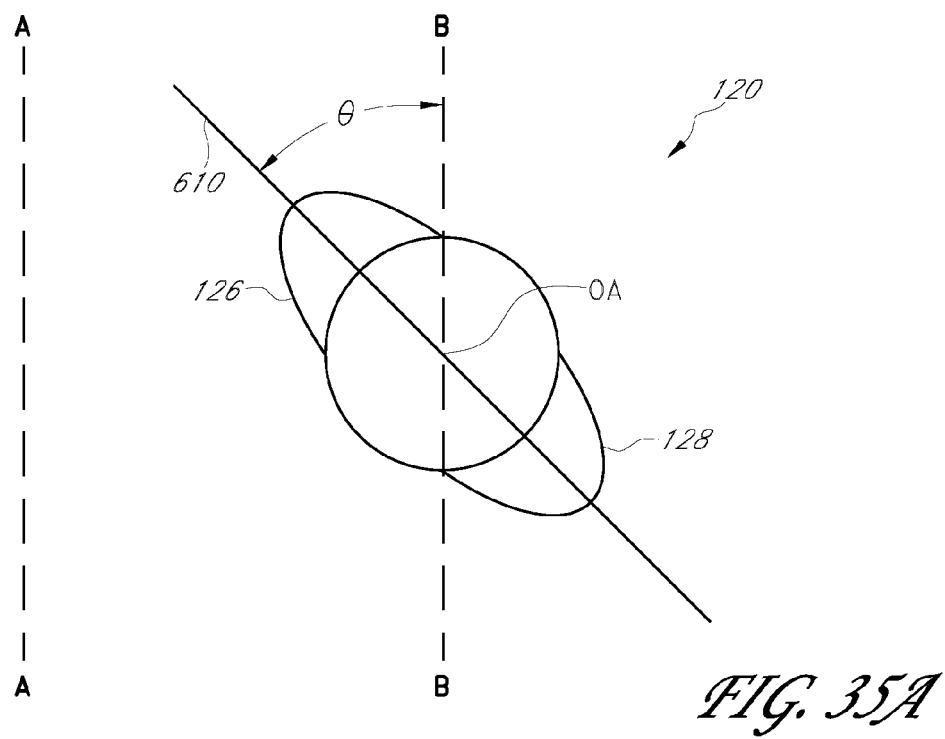
FIG. 35A is a schematic top view showing an initial orientation of a multiple-lens IOL in a home condition within a lens compactor.

FIG. 35A is a schematic top view showing an initial orientation of a multiple-lens IOL 120 in a home condition within a lens compactor. The IOL 120 comprises viewing elements 122, 124 and biasing members 126, 128. The IOL 120 shown in FIG. 35A may be generally similar to the IOL 120 depicted in FIGS. 2 and 33. In the home position the IOL 120 is disposed between the faces of the lens compactor in a substantially unstressed condition in which the optical axes of the viewing elements 122, 124 are substantially coincident with each other and/or with the optical axis (OA) of the IOL 120 itself.

The longitudinal bisection axis of the IOL 120 is indicated as line 610 in FIG. 35A. The line B-B shown in FIG. 35A is a line that is generally parallel to the delivery/injection axis A-A, but which is displaced laterally (or otherwise) from the delivery/injection axis A-A so as to intersect with the optical axis of the IOL 120. (Alternatively, the line B-B can be coincident with the injection axis A-A). In the embodiment shown in FIG. 35A, the IOL 120 is disposed within the lens compactor such that the longitudinal bisection axis 610 and the axis B-B are oriented at an initial orientation angle $\theta$. In some embodiments, the IOL 120 is disposed within the lens compactor such that the angle $\theta$ is approximately zero degrees or approximately 90 degrees. However, it is preferred, although not necessary, that the initial orientation angle $\theta$ be selected such that the longitudinal bisection axis 610 and the direction of the delivery axis B-B are generally non-parallel and non-perpendicular. For example, the angle $\theta$ may be in a range from about 15 degrees to about 20 degrees in some embodiments. In a preferred embodiment, the angle $\theta$ is about 17.5 degrees. Other angles are possible, including 5 degrees, 10 degrees, 25 degrees, 30 degrees, 45 degrees, etc. The angle $\theta$ selected for a particular IOL may depend upon the characteristics of the IOL including, for example, the cross-sectional shape of the IOL, the configuration of biasing members, etc. The angle $\theta$ may also depend on the characteristics of the lens compactor including, for example, the manner in which the compactor actuator moves the IOL from the home to the first position, the direction in which compaction forces are applied, etc. Accordingly, the initial orientation angle θ may be different for different IOLs and for different lens compactors. In certain embodiments, the angle θ advantageously is selected so that the viewing elements of the IOL 120 are more easily displaced and/or to avoid damaging the IOL and/or tearing or tangling the biasing members when the lens compactor is moved from the home position to the first compacted position.

Figure 35B:
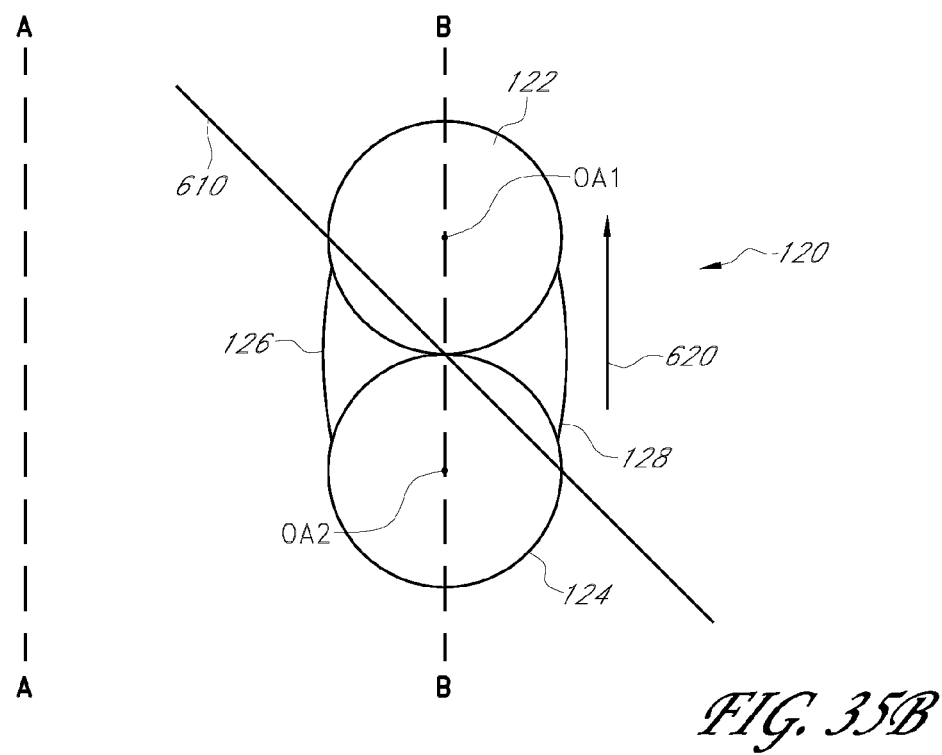
FIG. 35B is a schematic top view showing the IOL of FIG. 35A in a first compacted position.

FIG. 35B is a schematic top view showing the IOL 120 in a first compacted position. In some embodiments of the apparatus 200/400, the lens compactor moves from the home position to the first compacted position by advancing a compactor actuator 280/480 in a generally longitudinal direction along (or substantially parallel to) the axis B-B. In the first compacted position, the viewing elements 122, 124 are displaced generally longitudinally along the line B-B. An arrow 620 in FIG. 35B indicates the relative direction of displacement of the viewing elements 122, 124 after the IOL 120 has been moved into the first compacted position. Because the displacement is generally along the direction B-B, the longitudinal bisection axis 610 of the IOL 120 and the displacement direction 620 subtend an angle that is approximately equal to the initial orientation angle θ shown in FIG. 35A. In the first compacted position, the optical axes OA1 and OA2 of the viewing elements 122 and 124, respectively, are no longer coincident with each other or with the optical axis of the IOL 120. It is preferred, although not necessary, that the displacement be sufficiently large that the viewing elements 122, 124 do not overlap.

As described above with reference to FIGS. 15-18, a multiple-lens IOL can be moved from the home condition to the first compacted position by applying a displacement force generally in the direction of the arrow 620. For example, the upper lens compactor 240/440 may be advanced generally forward and downward, e.g., along the line B shown in FIG. 15, so as to cause the viewing elements 122, 124 to be displaced in the direction of the arrow 620. After the viewing elements 122, 124 are relatively displaced, the biasing members 126, 128 may be stretched slightly. By selecting the initial orientation angle θ as described herein, the IOL 120 in the first compacted position is advantageously configured for subsequent compaction.

After the IOL 120 is positioned in the first compacted position shown in FIG. 35B, in some embodiments the IOL 120 is moved to a second compacted position by moving the compactor actuator 280/480 in a generally lateral direction (e.g., in a direction generally perpendicular to the line B-B). In the second compacted position, the IOL 120 is in a folded, rolled, and/or crushed configuration suitable for passage through the delivery probe 206/406 (e.g., as described above with reference to FIGS. 17 and 18). The IOL 120 may then be delivered and inserted into the eye of the patient substantially as described above (e.g., by extruding the IOL 120 from the forward end of the delivery probe 206/406 by forward advancement of the driving member 290/490). By orienting the IOL 120 such that the longitudinal bisection axis 610 initially makes an angle θ with respect to the delivery axis B-B, the subsequent stage of moving the IOL 120 from the first compacted position to the second compacted position is facilitated because, for example, the biasing members 126, 128 are less likely to tangle or otherwise interfere with the folding/rolling/crushing of the IOL.

As shown and described with reference to FIGS. 35A and 35B, the IOL 120 may be disposed within the apparatus 200/400 such that the longitudinal bisection axis 610 makes a generally non-parallel and non-perpendicular angle with respect to the delivery or injection axis B-B. However, in other embodiments, the IOL 120 may be positioned within the apparatus 200/400 such that the longitudinal bisection axis 610 is substantially parallel to (or perpendicular to) the delivery/injection axis B-B. In such embodiments, a displacement force may be applied to the IOL at an angle φ that is generally non-parallel and non-perpendicular to the delivery/injection axis B-B. The displacement force moves the IOL 120 from a home condition to a first compacted position in which the viewing elements of the IOL are relatively displaced.

Figure 36A:
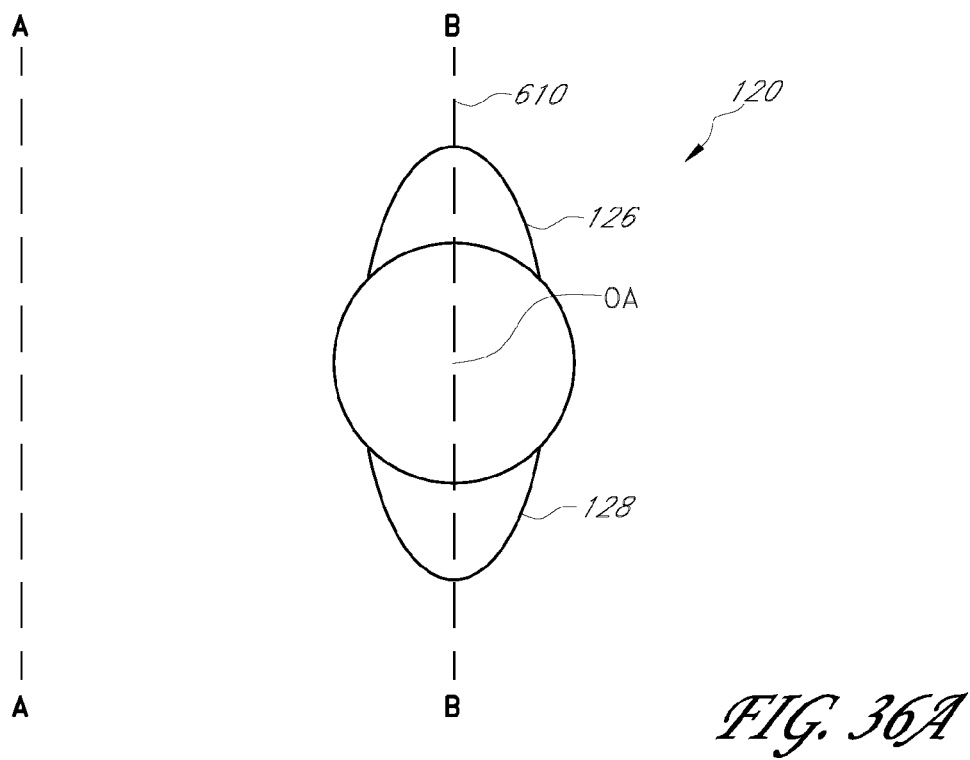
FIG. 36A is a schematic top view showing another initial orientation of a multiple-lens IOL in a home condition within a lens compactor.
Figure 36B:
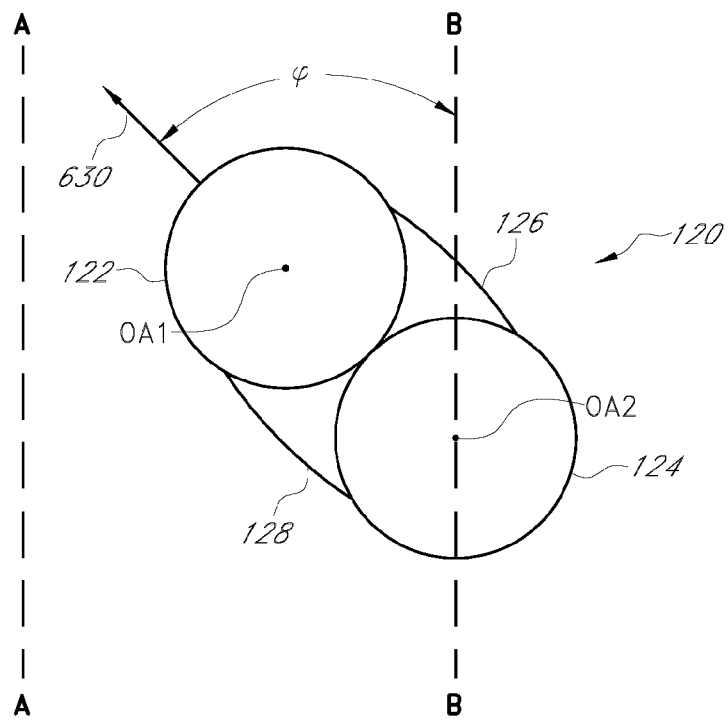
FIG. 36B is a schematic top view showing the IOL of FIG. 36A in a first compacted position.

FIG. 36A schematically illustrates a top view of an IOL 120 in a home condition in which the longitudinal bisection axis 610 is substantially parallel to the axis B-B (which is substantially parallel to, but displaced laterally from, the delivery/injection axis A-A). In this embodiment, the IOL 120 is moved from the home position to the first compacted position by applying a displacement force 630 that makes an angle φ with respect to the axis B-B. In some embodiments, the angle φ is in a range from about 15 degrees to about 20 degrees. In one preferred embodiment, the angle φ is approximately 17.5 degrees. Other angles are possible, including 5 degrees, 10 degrees, 25 degrees, 30 degrees, 45 degrees, etc. The angle φ may be selected so that the viewing elements 122, 124 are more readily displaced and/or to reduce tearing and/or tangling of the biasing members 126, 128. In some embodiments, the displacement force 630 is provided by advancing the upper (and/or lower) lens compactor so that the upper (and/or lower) engagement face urges the viewing elements 122, 124 in the direction shown by arrow 630. As described above with reference to FIGS. 16 and 35B, in the first compacted position the optical axes OA1 and OA2 of the viewing elements 122 and 124, respectively, are no longer coincident with each other or with the optical axis of the IOL 120. It is preferred, although not necessary, that the relative displacement be sufficiently large that the viewing elements 122, 124 do not overlap (see, e.g., FIG. 36B). As further described above with reference to FIGS. 17 and 18, in some embodiments the IOL 120 is subsequently moved into a second compacted position prior to delivery/insertion into the eye.

In other embodiments of the apparatus 200/400, various advantageous aspects described with reference to FIGS. 35A-36C may be used in combination. For example, in some embodiments, the IOL 120 is initially disposed within the lens compactor such that the longitudinal bisection axis 610 is at a non-parallel and non-perpendicular angle θ relative to the injection/delivery axis and a displacement force is applied to the IOL 120 at a non-parallel and non-perpendicular angle φ relative to the delivery/injection axis. In such embodiments, the angles θ and φ each may be in ranges from about 15 degrees to about 20 degrees. In some embodiments, the angles θ and φ are selected so that the sum of the angles, θ+φ, is in a range from about 15 degrees to about 20 degrees. In one preferred embodiment, the sum of the angles is about 17.5 degrees. In other embodiments, other angles may be selected.

A single-lens IOL, including (but not limited to) the IOL 100 described above, advantageously may be stored in a lens compactor in an initial configuration that provides easier compaction and/or delivery into the eye of a patient. In a similar manner to that described above, a longitudinal bisection axis can be suitably defined for the single-lens IOL. For example, in the IOL 100 shown in FIG. 1, a longitudinal bisection axis can be defined as coincident with a line passing through the radially outermost ends or portions of the haptics 104 and 106. The IOL 100 can be disposed in the apparatus 200/400 such that the longitudinal bisection axis of the IOL 100 is disposed at an initial orientation angle with respect to the injection/delivery axis. In certain embodiments, this initial angle is in a range from about 15 degrees to about 20 degrees, although other angles such as, for example, 5 degrees, 10 degrees, 30 degrees, etc. may be used.

As a further alternative, the injector (assigned the reference numeral 100) disclosed in U.S. Patent Application Publication No. 2005/0182419, published on Aug. 18, 2005, titled INJECTOR FOR INTRAOCULAR LENS SYSTEM, may be employed in place of the apparatus 200/400 in practicing the methods and apparatus disclosed herein in connection with FIGS. 33-36B. U.S. Patent Application Publication No. 2005/0182419 is hereby incorporated by reference herein in its entirety. In particular, the IOL 100 can be positioned within the injector 100 of the above-mentioned publication at an initial orientation angle θ with respect to the injection axis A-A of the injector 100 as discussed above, when in the home position or condition. The IOL 100, so positioned within the injector 100, can then be compacted with the injector 100 in the manner disclosed in the above-mentioned publication.

Various embodiments of the apparatus 200/400 disclosed herein advantageously facilitate delivery of an IOL into the eye of a patient without need for a physician to handle the IOL or manually load it into an insertion device. For example, the IOL may be positioned within the lens compactor (e.g., between the upper and lower lens compactors) of the apparatus 200/400 during manufacture/assembly of the apparatus. As described above, in some embodiments, the IOL is positioned within the lens compactor with an initial configuration and/or orientation that subsequently permits for easier compaction and delivery of the IOL. The apparatus 200/400, with the IOL thus disposed inside the lens compactor, may then be sterilized as a unit, either at the point of manufacture or at some downstream location. Where appropriate, the sterilized apparatus-IOL assembly may be contained in a sterile package, wrapper, bag, envelope, etc. in which the apparatus-IOL assembly may remain until arrival at the point (or time) of use. (The apparatus-IOL assembly may be sterilized before and/or after placement in the package, etc.) This further facilitates a simple point-of-use procedure for medical personnel involved in implanting the IOL contained in the apparatus 200/400: after opening (any) packaging, the physician, or other medical personnel, can compact and insert the IOL using the apparatus 200/400 as discussed above, without (any need for) removing the IOL from the apparatus. Accordingly, there is no need to handle the IOL or manually load it into an insertion device at the point of use, both of which can be difficult and tedious, and can compromise the sterility of the IOL.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An apparatus for delivering an accommodating intraocular lens to an eye, said apparatus comprising:
    an injector with a longitudinal injection passage having a longitudinal injection axis; and
    an accommodating intraocular lens having two interconnected viewing elements, said lens having an optical axis and a longitudinal bisection axis that is substantially perpendicular to the optical axis, the two viewing elements of said intraocular lens interconnected by no more than a first biasing member and a second biasing member, the first biasing member and the second biasing member disposed at opposite sides of the viewing elements, the longitudinal bisection axis defined between the first biasing member and the second biasing member along a line that substantially bisects said lens and at least one of said first and second biasing members;
    said injector having a member for moving said lens into said injection passage;
    said lens disposed within said injector with said longitudinal bisection axis of said lens at an angle which is non-parallel and non-perpendicular to said injection axis.

2. The apparatus of claim 1, wherein said lens is at said angle prior to movement of said member, and said member is operable to move in a direction non-perpendicular to said longitudinal bisection axis.

3. The apparatus of claim 1, wherein said member is operable to move in a displacement direction, and said longitudinal bisection axis is non-parallel and non-perpendicular to said displacement direction.

4. The apparatus of claim 1, wherein said longitudinal bisection axis comprises a transverse axis of said lens.

5. The apparatus of claim 1, wherein said lens comprises a line of reflection symmetry and said longitudinal bisection axis comprises said line of reflection symmetry.

6. The apparatus of claim 1, wherein the longitudinal bisection axis substantially bisects said lens and both of said first and second biasing members.

7. The apparatus of claim 1, wherein said angle is in a range from about 15 degrees to about 20 degrees.

8. The apparatus of claim 1, wherein said angle is about 17.5 degrees.

9. The apparatus of claim 1, wherein the longitudinal bisection axis bisects said lens into two substantially congruent portions.

10. A method for preparing an accommodating intraocular lens for delivery to an eye, said method comprising:
    providing an injector with a longitudinal injection passage having a longitudinal injection axis, and an accommodating intraocular lens having two interconnected viewing elements and a longitudinal bisection axis, said longitudinal bisection axis substantially perpendicular to an optical axis of said intraocular lens, said intraocular lens disposed within said injector, the two viewing elements of said intraocular lens interconnected by no more than a first biasing member and a second biasing member, the first biasing member and the second biasing member disposed at opposite sides of the viewing elements, the longitudinal bisection axis defined between the first biasing member and the second biasing member along a line that substantially bisects said lens and at least one of said first and second biasing members;
    initiating movement of one viewing element of said intraocular lens relative to the other viewing element thereof in an initial direction within said injector, the initial direction having a component in a plane perpendicular to said optical axis of said intraocular lens that is at an angle that is non-parallel and non-perpendicular to said longitudinal bisection axis prior to said movement or non-parallel and non-perpendicular to said longitudinal injection axis prior to said movement; and
    further moving said intraocular lens into said injection passage.

11. The method of claim 10, wherein said angle is in a range from about 15 degrees to about 20 degrees.

12. The method of claim 10, wherein said angle is about 17.5 degrees.

13. The method of claim 10, further comprising compacting said intraocular lens while said lens is disposed within said injector.

14. The method of claim 10, further comprising advancing said lens along said injection passage.

15. The method of claim 10, wherein the longitudinal bisection axis bisects said lens into two substantially congruent portions.

16. A method for preparing an accommodating intraocular lens for delivery to an eye, said method comprising:
providing an injector with a longitudinal injection passage having a longitudinal injection axis, and an accommodating intraocular lens having first and second interconnected viewing elements and a longitudinal bisection axis substantially perpendicular to an optical axis of said intraocular lens, said intraocular lens disposed within said injector, said longitudinal bisection axis defining an initial longitudinal axis direction prior to movement of the lens within the injector, the first and second viewing elements interconnected by no more than two pairs of biasing members, said intraocular lens having an axis of reflection symmetry, said longitudinal bisection axis defined along said axis of reflection symmetry;
applying an initial force to at least one of said viewing elements, said initial force having a force component in a plane perpendicular to the optical axis of said intraocular lens, said initial force applied in an initial direction such that the force component is at an angle that is non-parallel and non-perpendicular to said initial longitudinal axis direction or non-parallel and non-perpendicular to said longitudinal injection axis; and
moving said intraocular lens into said injection passage.

17. The method of claim 16, further comprising relatively displacing the first and the second viewing elements of the intraocular lens along a displacement direction having a displacement component in a plane perpendicular to the optical axis of said intraocular lens that is at a non-parallel and non-perpendicular displacement angle relative to said initial longitudinal axis direction.

18. The method of claim 17, wherein said displacement angle is in a range from about 15 degrees to about 20 degrees.

19. The method of claim 17, wherein said displacement angle is about 17.5 degrees.

20. The method of claim 16, wherein the first and the second viewing elements of the intraocular lens are interconnected by exactly one pair of oppositely disposed biasing members.

21. An apparatus for manipulating an accommodating intraocular lens having first and second viewing elements with respective optical axes that are substantially coaxial, said lens having a longitudinal axis substantially perpendicular to said substantially coaxial optical axes, the first and second viewing elements interconnected by no more than two pairs of biasing members, said intraocular lens having an axis of reflection symmetry, said longitudinal axis defined along said axis of reflection symmetry, said apparatus comprising:
an injector having a first configuration and a second configuration; and
a lens displacement member that is movable by a user to change the injector from the first configuration to the second configuration;
wherein in the first configuration the intraocular lens is disposed in the injector and the longitudinal axis of the lens defines an initial direction,
wherein in the second configuration the first and second viewing elements are relatively displaced such that a displacement direction is defined therebetween and such that the optical axes are not substantially coaxial, said displacement direction defined in a plane substantially perpendicular to said optical axes,
wherein the initial direction and the displacement direction define a non-zero and non-perpendicular angle therebetween.

22. The apparatus of claim 21, wherein the angle is in a range between about 15 degrees and 20 degrees.

23. The apparatus of claim 21, wherein the angle is about 17.5 degrees.

24. The apparatus of claim 21, wherein the first and the second viewing elements of the intraocular lens are interconnected by exactly one pair of oppositely disposed biasing members.

* * * * *